United States Patent
Yamamoto et al.

(10) Patent No.: US 10,545,159 B2
(45) Date of Patent: Jan. 28, 2020

(54) MANAGEMENT METHOD FOR A SAMPLE PROCESSING APPARATUS

(71) Applicant: Sysmex Corporation, Kobe-shi (JP)

(72) Inventors: Junzo Yamamoto, Kobe (JP); Shigeo Kanamori, Kobe (JP); Fumio Inoue, Kobe (JP); Ikuya Takenaka, Kobe (JP); Osamu Hirota, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 180 days.

(21) Appl. No.: 15/350,805

(22) Filed: Nov. 14, 2016

(65) Prior Publication Data

US 2017/0059598 A1 Mar. 2, 2017

Related U.S. Application Data

(60) Division of application No. 13/752,882, filed on Jan. 29, 2013, now Pat. No. 9,494,610, which is a (Continued)

(30) Foreign Application Priority Data

Jul. 30, 2010 (JP) ................................ 2010-172958

(51) Int. Cl.
*G01N 35/00* (2006.01)
*G16H 40/40* (2018.01)
*G16H 10/40* (2018.01)

(52) U.S. Cl.
CPC . *G01N 35/00623* (2013.01); *G01N 35/00722* (2013.01); *G01N 35/00871* (2013.01); *G16H 10/40* (2018.01); *G16H 40/40* (2018.01)

(58) Field of Classification Search
CPC ................................................. G01N 35/00623
(Continued)

(56) References Cited

U.S. PATENT DOCUMENTS 6,579,717 B1 6/2003 Matsubara et al.
6,644,136 B1 11/2003 Carney et al.
(Continued)

FOREIGN PATENT DOCUMENTS

| EP | 0 672 906 A | 9/1995 |
| JP | 2000-275207 A | 10/2000 |

(Continued)

OTHER PUBLICATIONS

International Search Report for International Application No. PCT/JP2011/004176, dated Aug. 30, 2011, 2 pages.

*Primary Examiner* — Justin Seo
*Assistant Examiner* — Rodney T Frank
(74) *Attorney, Agent, or Firm* — Brinks Gilson & Lione

(57) ABSTRACT

A managing method for a sample processing apparatus involving the sample processing apparatus and a management apparatus. The method includes requesting an approval of self-adjustment to the management apparatus from the sample processing apparatus before performing a self-adjustment. Informing the sample processing apparatus of approval of request from the management apparatus, when approving the sample processing apparatus to perform the self-adjustment, and performing a self-adjustment by the sample processing apparatus when the sample processing apparatus is informed that the request has been approved.

20 Claims, 12 Drawing Sheets

Related U.S. Application Data continuation of application No. PCT/JP2011/004176, filed on Jul. 25, 2011.

(58) Field of Classification Search
    USPC .................................................. 73/863.01
    See application file for complete search history.

(56) References Cited

U.S. PATENT DOCUMENTS

| | | | |
|---|---|---|---|
| 9,494,610 B2* | 11/2016 | Yamamoto | ....... G01N 35/00623 |
| 2004/0216009 A1 | 10/2004 | Kihara | |
| 2007/0016104 A1 | 1/2007 | Jansen et al. | |
| 2008/0241937 A1 | 10/2008 | Wakamiya et al. | |
| 2010/0121170 A1 | 5/2010 | Rule | |

FOREIGN PATENT DOCUMENTS

| | | |
|---|---|---|
| JP | 2004-286663 A | 10/2004 |
| JP | 2008-046095 A | 2/2008 |
| JP | 2008-072418 A | 3/2008 |
| JP | 2008-249600 A | 10/2008 |
| JP | 2010-164432 A | 7/2010 |

* cited by examiner

F I G. 1
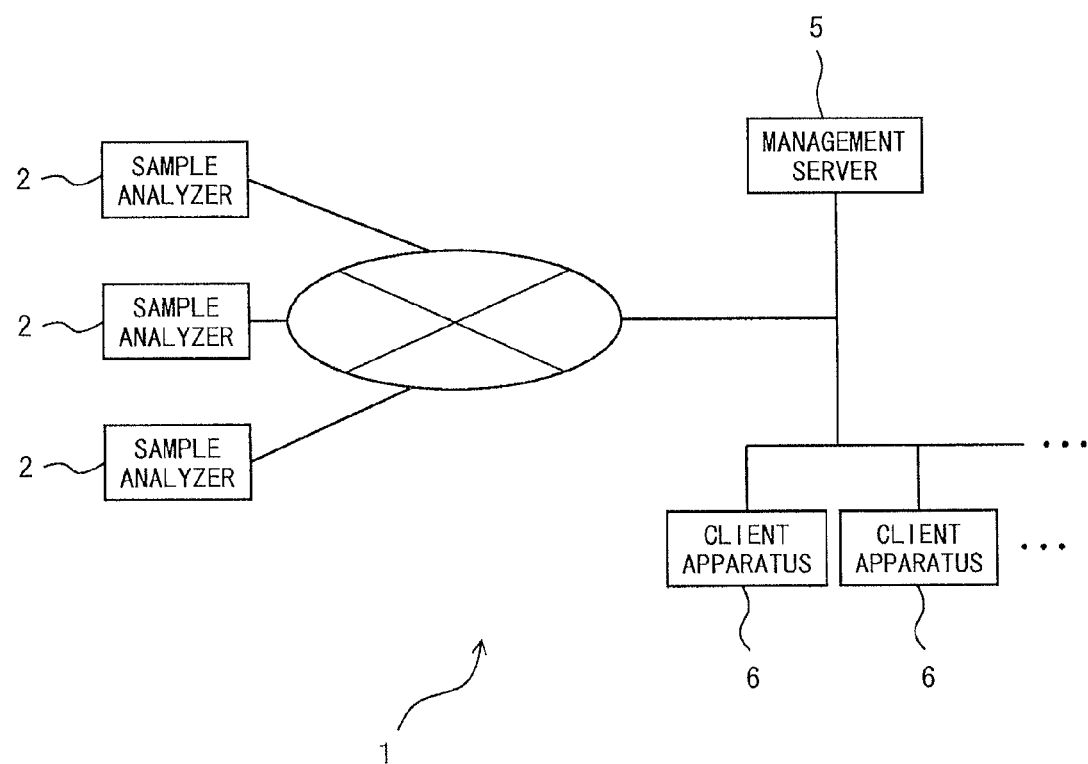

MANAGEMENT METHOD FOR A SAMPLE PROCESSING APPARATUS

RELATED APPLICATIONS

This application is a divisional patent application of U.S. application Ser. No. 13/752,882, filed Jan. 29, 2013, which is a continuation of PCT/JP2011/004176 filed on Jul. 25, 2011, which claims priority to Japanese Application No. 2010-172958 filed on Jul. 30, 2010. The entire contents of these applications are incorporated herein by reference.

BACKGROUND

The present invention relates to management systems for sample processing apparatuses which process clinical samples such as blood and urine, sample processing apparatuses and management apparatuses, and management methods.

There are known sample processing apparatuses which process samples, such as blood cell counters, blood coagulation measurement apparatuses, immunoassay apparatuses, gene amplification measurement apparatuses, urine qualitative analyzers, urine formed element analyzers, biochemical analyzers, and blood smear preparation apparatuses. When abnormality has occurred in such a sample processing apparatus, there may be a case where a technician in charge of maintenance has to take a countermeasure against the abnormality.

Japanese Laid-Open Patent Publication No. 2004-286663 discloses an automatic analyzer in which when abnormality has occurred in the automatic analyzer, a notification e-mail is generated and the notification e-mail is transmitted to the person in charge. The e-mail transmitted from this automatic analyzer includes information, such as the data under analysis and the analysis condition, as a message or an attached file. The person in charge reads this e-mail by using, for example, a personal computer, a mobile phone, or a personal digital assistant, understands the status of the automatic analyzer and the state of the fault that occurred, and transmits a reply mail to the notification e-mail, the reply mail containing a command for causing the automatic analyzer to perform an operation for taking a countermeasure against the failure. An automatic analyzer 1 performs the operation for taking a countermeasure against the failure, by extracting the command from the received reply mail and performing the command. Examples of operations for taking countermeasures against failures disclosed in Japanese Laid-Open Patent Publication No. 2004-286663 include performing, after analysis is resumed and analysis condition has become stable, analysis from the beginning again, column cleaning, removing bubbles, preprocessing, and the like.

SUMMARY

However, in the automatic analyzer described in Patent Literature 1 above, the person in charge needs to examine a countermeasure against the failure and transmit a command for an operation as a countermeasure by an e-mail, which is a great burden on the person in charge. Further, there are individual differences among automatic analyzers, and optimum set values are different in each automatic analyzer. However, in Patent Literature 1 described above, it is difficult for the person in charge who is in a remote place to designate set values unique to the automatic analyzer in which the failure has occurred. Further, it is difficult to restore the automatic analyzer from the failure that requires adjustment of values to set values that are different in each automatic analyzer.

The present invention has been made in view of the above problem. A main object of the present invention is to provide a sample processing apparatus management system, sample processing apparatuses, a management apparatus, and a management method that can accurately and easily adjust the respective sample processing apparatuses irrespective of their individual differences.

In order to solve the problems described above, a sample processing apparatus management system according to an aspect of the present invention is a sample processing apparatus management system comprising: a sample processing apparatus which processes samples; and a management apparatus communicably connected to the sample processing apparatus, the sample processing apparatus comprising: a self-adjustment section which performs self-adjustment; and a first communication section which requests an approval of the self-adjustment, before the self-adjustment by the self-adjustment section is performed, the management apparatus comprising: a determination section which determines whether to approve the request; and a second communication section which informs, when approving the request to perform the self-adjustment, the sample processing apparatus of approval of the request, wherein the sample processing apparatus is configured to perform, when informed that the request has been approved, the self-adjustment by the self-adjustment section.

In this aspect, the sample processing apparatus may further include an event detection section which detects an event for starting the self-adjustment by the self-adjustment section, and the first communication section may be configured to request the approval when the event detection section has detected the event.

In the above aspect, the sample processing apparatus may further include an abnormality detector which detects abnormality in the sample processing apparatus, and the event detection section may be configured to detect, as the event, the detection of the abnormality by the abnormality detector.

In the above aspect, the sample processing apparatus may further include a type determination section which determines a type of the event detected by the event detection section, the first communication section may be configured to request the approval when the type determination section has determined that the type of the event detected by the event detection section is a first type, and configured not to request the approval when the type determination section has determined that the type of the event detected by the event detection section is a second type which is different from the first type, and the sample processing apparatus may be configured such that, in a case where the type determination section has determined that the type of the event detected by the event detection section is the first type, the sample processing apparatus performs the self-adjustment by the self-adjustment section when informed that the request has been approved, and in a case where the type determination section has determined that the type of the event detected by the event detection section is the second type, the sample processing apparatus performs the self-adjustment by the self-adjustment section, without waiting for the approval.

In the above aspect, the sample processing apparatus may further include an adjustment value generation section which generates an adjustment value for the sample processing apparatus, and the self-adjustment section may be configured to perform the self-adjustment of the sample processing apparatus to the adjustment value generated by the adjustment value generation section.

In the above aspect, the sample processing apparatus may further include: a measurement unit which measures samples; a memory in which calibration information for calibrating a measurement result is stored; and a conversion section which converts a measurement result obtained by the measurement unit, based on the calibration information stored in the memory, the adjustment value generation section may be configured to generate calibration information as the adjustment value for the sample processing apparatus, based on a measurement result obtained by the measurement unit measuring a calibration information generation specimen, and the self-adjustment section may be configured to perform the self-adjustment of the sample processing apparatus, by storing in the memory the calibration information generated by the adjustment value generation section.

In the above aspect, the sample processing apparatus may further include an operation mechanism whose position can be adjusted and which performs an operation regarding sample measurement, the adjustment value generation section may be configured to generate a position adjustment amount for the operation mechanism as the adjustment value for the sample processing apparatus, and the self-adjustment section may be configured to perform the self-adjustment of the sample processing apparatus by adjusting the position of the operation mechanism based on the position adjustment amount generated by the adjustment value generation section.

In the above aspect, the operation mechanism may be configured to be able to move to a specific position for sample measurement, and the adjustment value generation section may be configured to generate the position adjustment amount for positioning the operation mechanism at the specific position.

In the above aspect, the operation mechanism may be a dispensing mechanism which moves to an aspirating position for aspirating a sample or a reagent and aspirates the sample or the reagent, and which moves to a discharging position for discharging a sample or a reagent and discharges the sample or the reagent.

In the above aspect, the first communication section may be configured to request the approval with transmitting specifying information for specifying a user who uses the sample processing apparatus, and the determination section may be configured to determine whether to approve the request, based on the specifying information.

In the above aspect, the first communication section may be configured to request the approval with transmitting the adjustment value generated by the adjustment value generation section, and the determination section may be configured to determine whether to approve the request, based on the adjustment value.

Further, a sample processing apparatus according to an aspect of the present invention is a sample processing apparatus which is communicably connected to a management apparatus and which processes samples, the sample processing apparatus including: a self-adjustment section which performs self-adjustment; and a communication section which requests, to the management apparatus, an approval of the self-adjustment, before the self-adjustment by the self-adjustment section is performed, wherein the sample processing apparatus is configured to perform, when informed that request has been approved, the self-adjustment by the self-adjustment section.

Further, a management apparatus according to an aspect of the present invention is a management apparatus communicably connected to a sample processing apparatus which processes samples, the management apparatus including: a determination section which determines, when an approval of a self-adjustment has been requested from the sample processing apparatus, whether to approve the request; and a communication section which informs, when the determination section has determined to approve the request, the sample processing apparatus of approval of the request.

Further, a management method according to an aspect of the present invention is a managing method for a sample processing apparatus by using the sample processing apparatus and a management apparatus, the method including: requesting, before performing self-adjustment, an approval of self-adjustment to the management apparatus from the sample processing apparatus; informing, when approving the sample processing apparatus to perform the self-adjustment, the sample processing apparatus of approval of request, from the management apparatus; and performing self-adjustment by the sample processing apparatus when the sample processing apparatus is informed that the request has been approved In the above aspect, the management method may further include an event detection step of the sample processing apparatus detecting an event for starting the self-adjustment, wherein the request of approval is made when the event has been detected.

In the above aspect, the event detection step may be configured to include a step of detecting, as the event, abnormality in the sample processing apparatus.

In the above aspect, the management method may further include a determination step of the sample processing apparatus determining a type of the event detected in the event detection step, wherein the self-adjustment step may be configured to perform, when the type of the event is a type of an event for which the self-adjustment should be performed without waiting for the approval, the self-adjustment without waiting for the approval.

According to the management system, the sample processing apparatuses and the management apparatus, and the management method according to the present invention, it is possible to accurately and easily adjust the respective sample processing apparatuses irrespective of their individual differences, compared to conventional ones.

BRIEF DESCRIPTION OF THE DRAWING

FIG. 1 is a schematic diagram showing a configuration of a management system according to embodiment 1.

DETAILED DESCRIPTION OF THE PREFERRED EMBODIMENTS

Hereinafter, preferred embodiments of the present invention will be described with reference to the drawings.

Embodiment 1

[Configuration of Management System]

FIG. 1 is a schematic diagram showing a configuration of a management system 1 according to the present embodiment. The management system 1 includes sample analyzers 2, 2, . . . , provided in a user facility such as a hospital or a test center, and a management server 5 provided in a maintenance service provider facility such as a manufacturer of the sample analyzers 2 that performs maintenance of the sample analyzers 2. The sample analyzers 2, 2, . . . and the management server 5 are data-communicably connected to each other via a communication network such as the Internet or dedicated lines. Further, the management server 5 is data-communicably connected, via a LAN, to a plurality of client apparatuses 6 that are used by technicians of the maintenance service provider.

<Configuration of Sample Analyzer>

Figure 2:
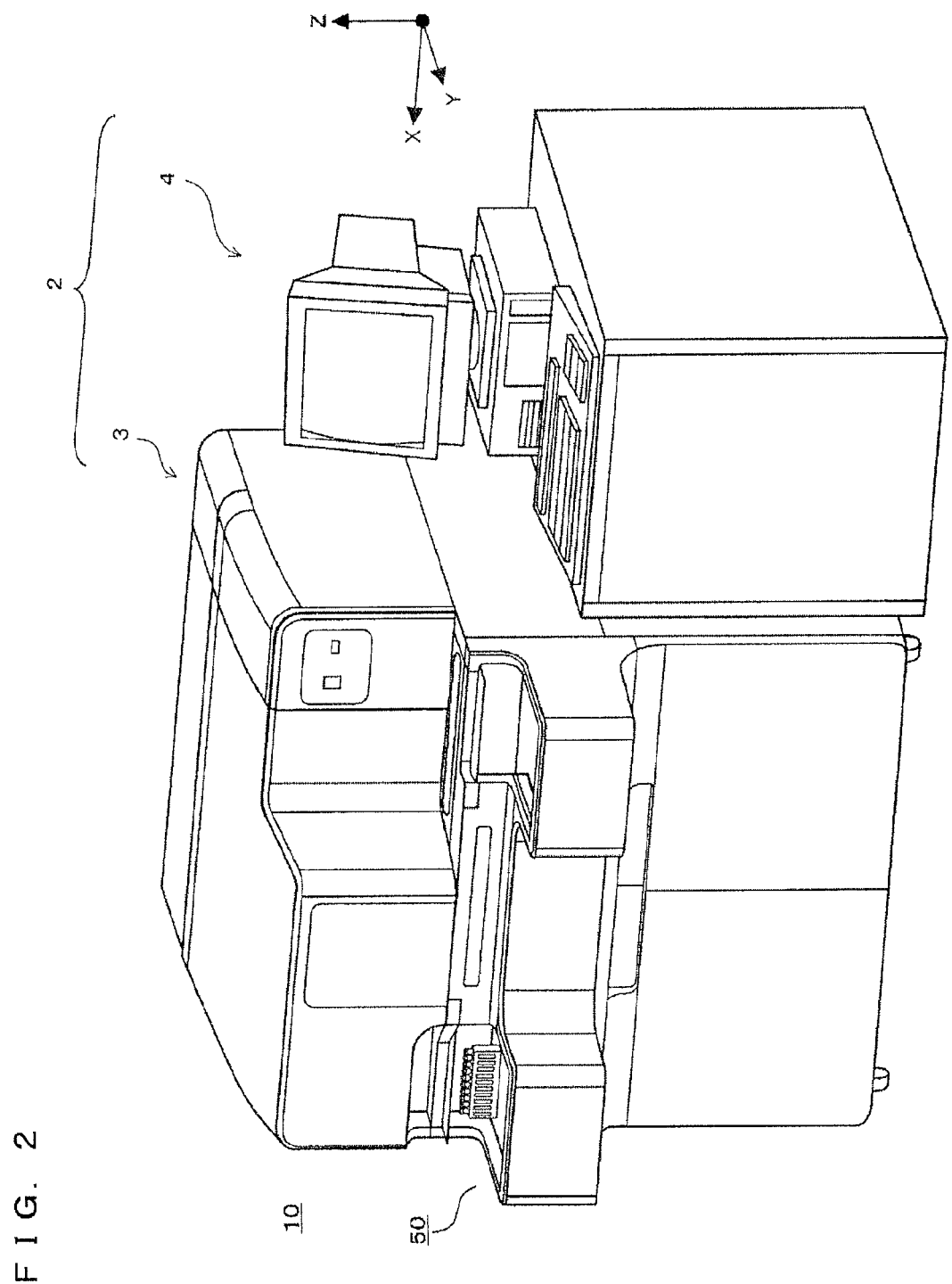
FIG. 2 is a perspective view showing a structure of a sample analyzer according to embodiment 1.

FIG. 2 is a perspective view showing a structure of the sample analyzer 2 according to the present embodiment. The sample analyzer 2 includes a measurement unit 3 which performs optical measurement on components contained in a clinical sample (blood), and an information processing unit 4 which analyzes measurement data obtained by the measurement unit 3 and provides operation instructions to the measurement unit 3.

Figure 3:
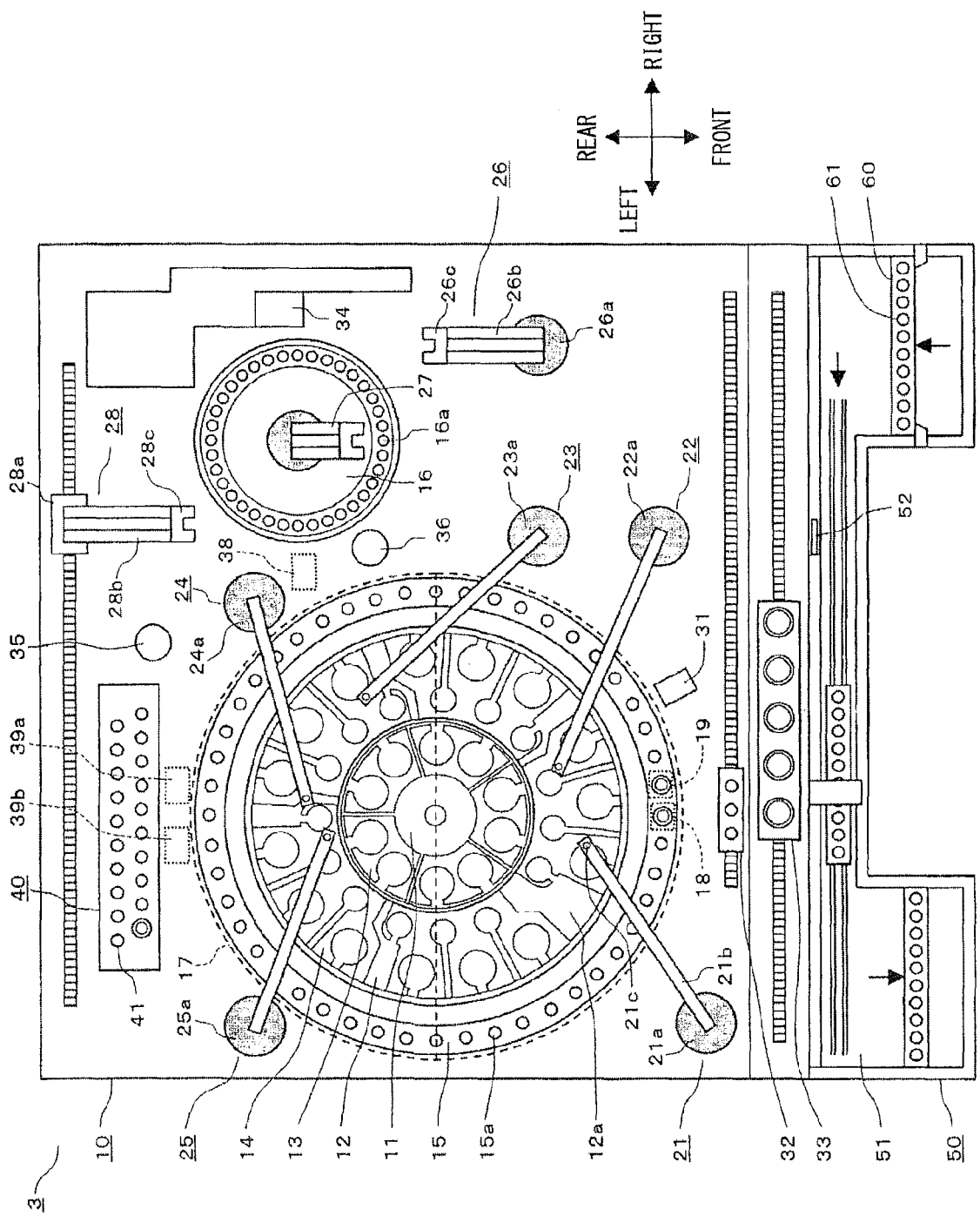
FIG. 3 is a plan view showing a schematic configuration of the inside of a measurement unit, seen from above.

FIG. 3 is a plan view showing a schematic configuration of the inside of the measurement unit 3, seen from above. The measurement unit 3 includes a measurement section 10, a detection unit 40, and a transporting unit 50.

The measurement section 10 includes a first reagent table 11, a second reagent table 12, a first container rack 13, a second container rack 14, a cuvette table 15, a heating table 16, a table cover 17, a first sample dispensing unit 21, a second sample dispensing unit 22, a first reagent dispensing unit 23, a second reagent dispensing unit 24, a third reagent dispensing unit 25, a first catcher unit 26, a second catcher unit 27, a third catcher unit 28, a reagent bar code reader 31, a cuvette transporter 32, a diluent transporter 33, a cuvette hole 34, and disposal holes 35 and 36.

Each of the first reagent table 11, the second reagent table 12, the cuvette table 15, and the heating table 16 is a circular table, and is independently and rotationally driven in both clockwise and counter-clockwise directions. These tables are rotationally driven by a plurality of stepping motors (not shown), respectively, that are provided on the rear side of the bottom of the measurement unit.

As shown in FIG. 3, five first container racks 13 are removably provided on the top surface of the first reagent table 11, and five second container racks 14 are removably provided on the top surface of the second reagent table 12. Holders for holding reagent containers are formed in each of the first container racks 13 and the second container racks 14. A bar code label is attached to each of the reagent containers held in the first reagent table 11 and the second reagent table 12. On the bar code label, printed is a bar code which stores reagent information such as the type of the reagent, the lot number, the expiration date, and the like. The bar code of each reagent container is read by the bar code reader 31.

As shown in FIG. 3, each of the cuvette table 15 and the heating table 16 is provided with a plurality of cuvette holding holes 15a (16a), along the periphery thereof. After cuvettes are set in the cuvette holding holes 15a (16a), the cuvettes are to be moved, in accordance with the rotation of the cuvette table 15 (the heating table 16), along the periphery thereof. The heating table 16 heats cuvettes set in the holding holes 16a, at a predetermined temperature.

Figure 4:
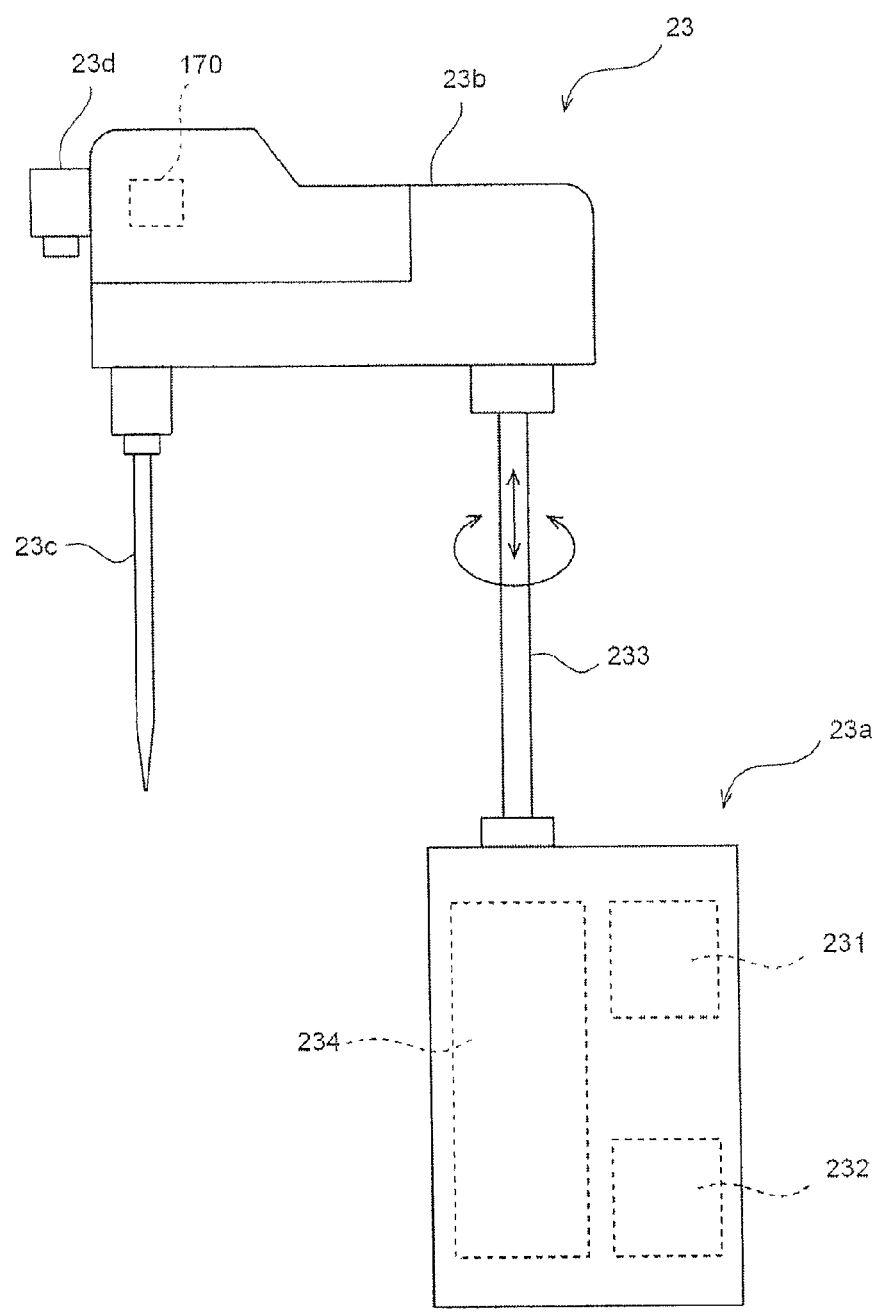
FIG. 4 is a side view showing a structure of a first reagent dispensing unit.

FIG. 4 is a side view showing a structure of the first reagent dispensing unit 23. As shown in FIG. 4, the first reagent dispensing unit 23 includes a driving section 23a, an arm 23b, and a pipette 23c. The driving section 23a includes a rotation motor 231, an ascent/descent motor 232, and a transmission mechanism 234 which transmits power of the rotation motor 231 and the ascent/descent motor 232 to a shaft 233. The transmission mechanism 234 includes: a belt transmission mechanism, a gear mechanism, or the like that decreases the rotation power of the rotation motor 231 and transmits the resultant power to the shaft 233; and a belt transmission mechanism, a rack-and-pinion mechanism, or the like that converts the rotation power of the ascent/descent motor 232 to linear power in the up-down direction and transmits the resultant power to the shaft 233. The rotation direction and the rotation amount of the rotation motor 231 is detected by a rotary encoder 235, and the rotation direction and the rotation amount of the ascent/descent motor 232 (that is, the up-down moving direction and the up-down moving amount of the pipette 23c) is detected by a rotary encoder 236.

Figure 5:
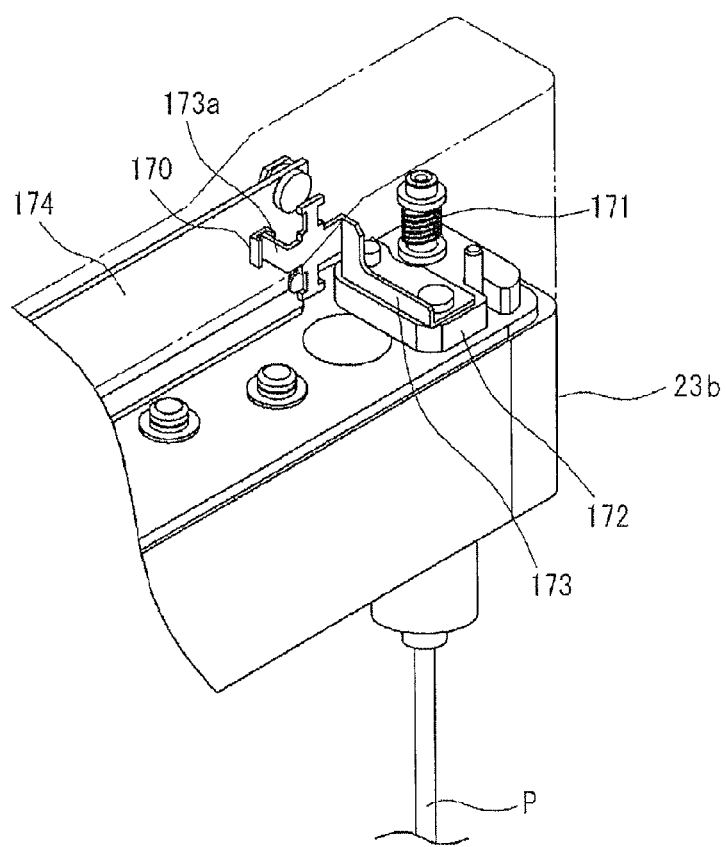
FIG. 5 is a perspective view showing a structure of a portion of an arm.

FIG. 5 is a perspective view showing a structure of a portion of the arm 23b. FIG. 5 shows the arm 23b whose inside is exposed by removing its top cover (shown by two-dot chain lines). A pipette P is supported by the arm 23b so as to be able to move (slide) in the up-down direction, and downward movement of the pipette P is restricted to a predetermined range. Further, the pipette P is under downward force from a force-applying member 171 composed of a helical compression spring. The arm 23b is provided with a base 172 which is movable in the up-down direction along with the pipette P. A detection member 173 is mounted on the base 172. The arm 23b is provided with a circuit board 174 so as to stand therein, and a collision detection sensor 170 is attached to the circuit board 174.

The collision detection sensor 170 includes a transmissive sensor that has a phototransmitter and a photoreceiver. The detection member 173 is provided with a light blocking plate 173a arranged between the phototransmitter and the photoreceiver of the collision detection sensor 170. The light blocking plate 173a blocks light in the collision detection sensor 170 in a normal state, thereby setting the collision detection sensor 170 to an off state. When the pipette P descends and collides with an obstacle, the pipette P is raised relative to the arm 23b, and the light blocking plate 173a is also raised via the base 172, whereby blocking light in the collision detection sensor 170 is canceled. Accordingly, when the collision detection sensor 170 is turned on, a measurement controller 140 detects that the pipette P has collided with an obstacle.

The first reagent dispensing unit 23 includes a camera 23d which includes an imaging sensor such as a CCD. The camera 23d is attached to an end of the arm 23b and can take an image of an area therebelow including the pipette P. Since the camera 23d is fixed to the arm 23b, even when the arm 23b is moved, the positional relationship between the camera 23d and the pipette P is not changed, whereby the camera 23d is allowed to take an image of an area always including the tip of the pipette P.

It should be noted that the configurations of the first sample dispensing unit 21, the second sample dispensing unit 22, the second reagent dispensing unit 24, and the third reagent dispensing unit 25 are similar to that of the first reagent dispensing unit 23, and thus, description thereof will be omitted.

With reference back to FIG. 3, the first catcher unit 26 includes: a support 26a which supports an arm 26b; the arm 26b which is able to extend/contract; and a grip portion 26c. The support 26a is rotationally driven by a stepping motor (not shown) provided on the rear side of the bottom of the measurement unit. The grip portion 26c is attached to the tip of the arm 26b, and can grip a cuvette. It should be noted that the second catcher unit 27 is also configured similarly to the first catcher unit 26, and is rotated by a stepping motor (not shown).

As shown in FIG. 3, the third catcher unit 28 includes: a support 28a which supports an arm 28b; the arm 28b which is able to extend/contract; and a grip portion 28c attached to the tip of the arm 28b. The support 28a is driven along a rail arranged in the left-right direction. The grip portion 28c can grip a cuvette.

The cuvette transporter 32 and the diluent transporter 33 are driven in the left-right direction on rails, respectively. Further, the cuvette transporter 32 is provided with holes for holding cuvettes and the diluent transporter 33 is provided with holes for holding diluent containers.

The cuvette hole 34 is always supplied with a new cuvette. A new cuvette is set in a hole for holding a cuvette in the cuvette transporter 32 or a cuvette holding hole 15a in the cuvette table 15, by the first catcher unit 26 or the second catcher unit 27, respectively. The disposal holes 35 and 36 are holes into which cuvettes are discarded for which analyses have been ended and which are no more needed.

Twenty holding holes 41 for holding cuvettes are formed in the top surface of the detection unit 40. A detector (not shown) is provided on the rear side of the bottom of the detection unit 40. When a cuvette is set in a holding hole 41, optical information of the measurement specimen in the cuvette is detected by the detector.

The transporting unit 50 includes a transport path 51, and a sample bar code reader 52. A pre-analysis rack holding area is provided on a right portion, a transportation area is provided in the middle, and a post-analysis rack holding area is provided on a left portion, on the bottom surface of the transport path 51. The transport path 51 is formed in a U-shape. The sample bar code reader 52 reads the bar code of a bar code label attached to a sample container 61 accommodated in a sample rack 60 being transported in the transportation area.

Figure 6:
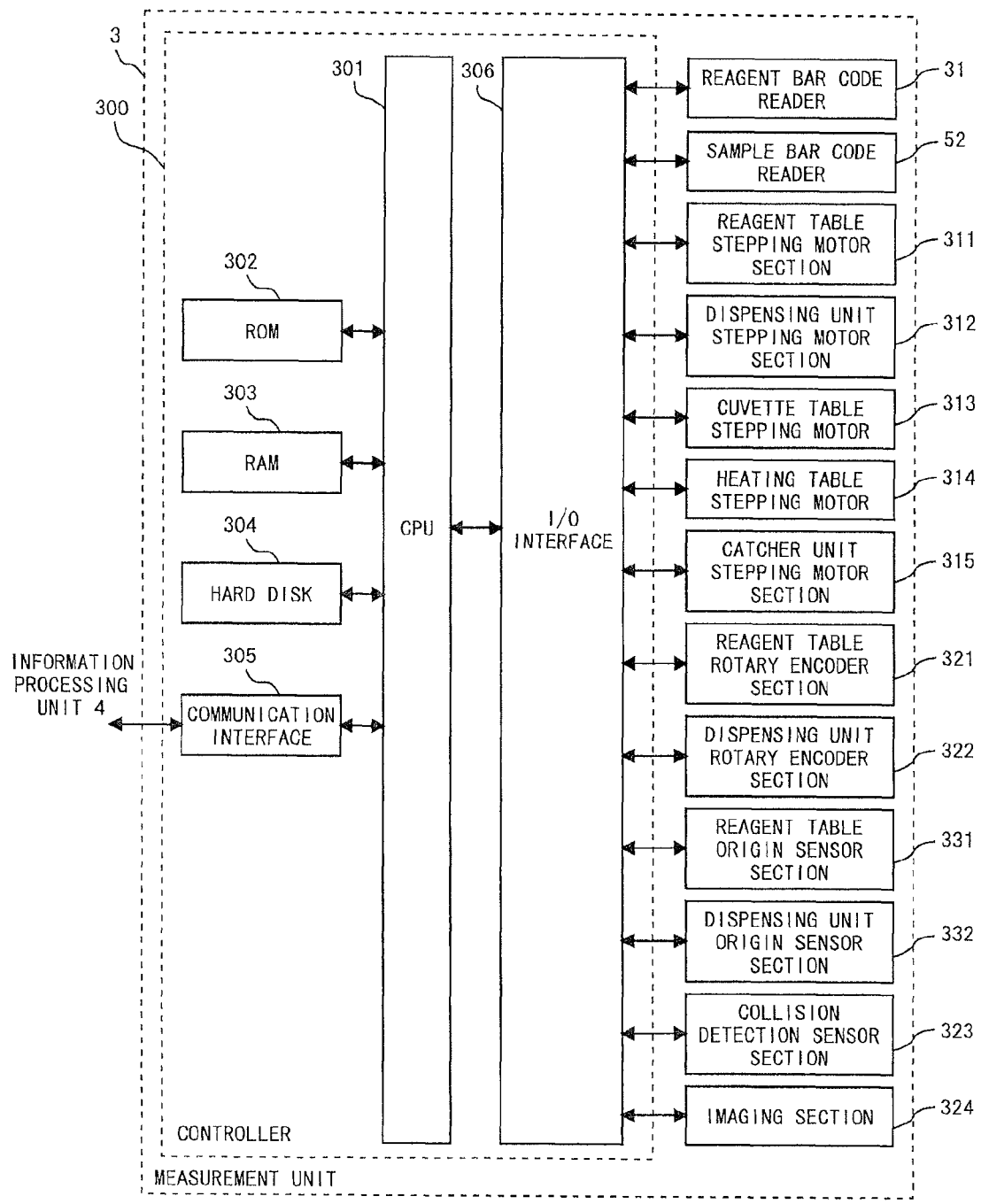
FIG. 6 is a block diagram showing a circuit configuration of a measurement unit.

FIG. 6 is a block diagram showing a circuit configuration of the measurement unit 3.

The measurement unit 3 includes a controller 300, the reagent bar code reader 31, the sample bar code reader 52, a reagent table stepping motor section 311, a dispensing unit stepping motor section 312, a cuvette table stepping motor 313, a heating table stepping motor 314, a catcher unit stepping motor section 315, a reagent table rotary encoder section 321, a dispensing unit rotary encoder section 322, a collision detection sensor section 323, a reagent table origin sensor section 331, a dispensing unit origin sensor section 332, and an imaging section 324. The controller 300 includes a CPU 301, a ROM 302, a RAM 303, a hard disk 304, a communication interface 305, and an I/O interface 306.

The CPU 301 executes computer programs stored in the ROM 302 and computer programs loaded onto the RAM 303. The RAM 303 is used for reading computer programs stored in the ROM 302 and the hard disk 304. Further, the RAM 303 is also used as a work area for the CPU 301 when the CPU 301 executes these computer programs. Various computer programs to be executed by the CPU 301 and data used in the execution of the computer programs, such as an operating system and application programs, are installed in the hard disk 304. That is, control programs for causing the CPU 301 to control sections of the measurement unit 3 are installed in the hard disk 304. Further, the communication interface 305 allows data to be transmitted/received to/from the information processing unit 4.

Further, the CPU 301 controls, via the I/O interface, the reagent bar code reader 31, the sample bar code reader 52, the reagent table stepping motor section 311, the dispensing unit stepping motor section 312, the reagent table rotary encoder section 321, the dispensing unit rotary encoder section 322, the collision detection sensor section 323, the reagent table origin sensor section 331, and the dispensing unit origin sensor section 332.

The reagent table stepping motor section 311 includes a plurality of stepping motors that rotationally drive the first reagent table 11 and the second reagent table 12 independently of each other. The dispensing unit stepping motor section 312 includes the rotation motor 231 and the ascent/descent motor 232 of the first reagent dispensing unit 23 described above, and respective rotation motors and ascent/descent motors of the first sample dispensing unit 21, the second sample dispensing unit 22, the second reagent dispensing unit 24, and the third reagent dispensing unit 25. These rotation motors and ascent/descent motors are stepping motors.

The cuvette table stepping motor 313 is implemented by a stepping motor that rotationally drives the cuvette table 15. The heating table stepping motor 314 is implemented by a stepping motor that rotationally drives the heating table 16. The catcher unit stepping motor section 315 includes a plurality of stepping motors that respectively rotate the first catcher unit 26 and the second catcher unit 27.

The reagent table rotary encoder section 321 includes a plurality of rotary encoders that can respectively and individually detect rotation directions and rotation amounts of the plurality of stepping motors included in the reagent table stepping motor section 311. The reagent table origin sensor section 331 includes a plurality of origin sensors that respectively and individually detect that rotational positions of the plurality of stepping motors included in the reagent table stepping motor section 311 are at their origin positions. By receiving output signals from the reagent table rotary encoder section 321 and the reagent table origin sensor section 331, the CPU 301 can recognize how many degrees each of the first reagent table 11 and the second reagent table 12 has rotated in the clockwise direction or counter-clockwise direction from its origin position.

The dispensing unit rotary encoder section 322 includes the rotary encoders 235 and 236 of the first reagent dispensing unit 23 described above and respective rotary encoders of the first sample dispensing unit 21, the second sample dispensing unit 22, the second reagent dispensing unit 24, and the third reagent dispensing unit 25. That is, the dispensing unit rotary encoder section 322 includes a plurality of rotary encoders that can respectively and individually detect rotation directions and rotation amounts of the plurality of stepping motors included in the dispensing unit stepping motor section 312. The dispensing unit origin sensor section 332 includes a plurality of origin sensors that respectively and individually detect that rotational positions of the plurality of stepping motors included in the dispensing unit stepping motor section 312 are at their origin positions. By receiving output signals from the dispensing unit rotary encoder section 322 and the dispensing unit origin sensor section 332, the CPU 301 can recognize how many degrees each of the arm 21b, 22b, 23b, 24b, and 25b of the first sample dispensing unit 21, the second sample dispensing unit 22, the first reagent dispensing unit 23, the second reagent dispensing unit 24, and the third reagent dispensing unit 25 has rotated in the clockwise direction or counter-clockwise direction from its origin position in the rotation direction, and how much the arm has moved upward or downward from its origin position (reference height) in the height direction.

Further, the collision detection sensor section 323 includes the collision detection sensor 170 of the first reagent dispensing unit 23 described above and respective collision detection sensors of the first sample dispensing unit 21, the second sample dispensing unit 22, the second reagent dispensing unit 24, and the third reagent dispensing unit 25. By receiving output signals from the collision detection sensor section 323, the CPU 301 can recognize whether each of the pipette 21c, 22c, 23c, 24c, and 25c of the first sample dispensing unit 21, the second sample dispensing unit 22, the first reagent dispensing unit 23, the second reagent dispensing unit 24, and the third reagent dispensing unit 25 has collided with an obstacle.

Further, the imaging section 324 includes the camera 23d of the first reagent dispensing unit 23 described above and respective cameras of the first sample dispensing unit 21, the second sample dispensing unit 22, the second reagent dispensing unit 24, and the third reagent dispensing unit 25. The CPU 301 can receive an output signal (image signal) from each of the cameras included in the imaging section 324.

Figure 7:
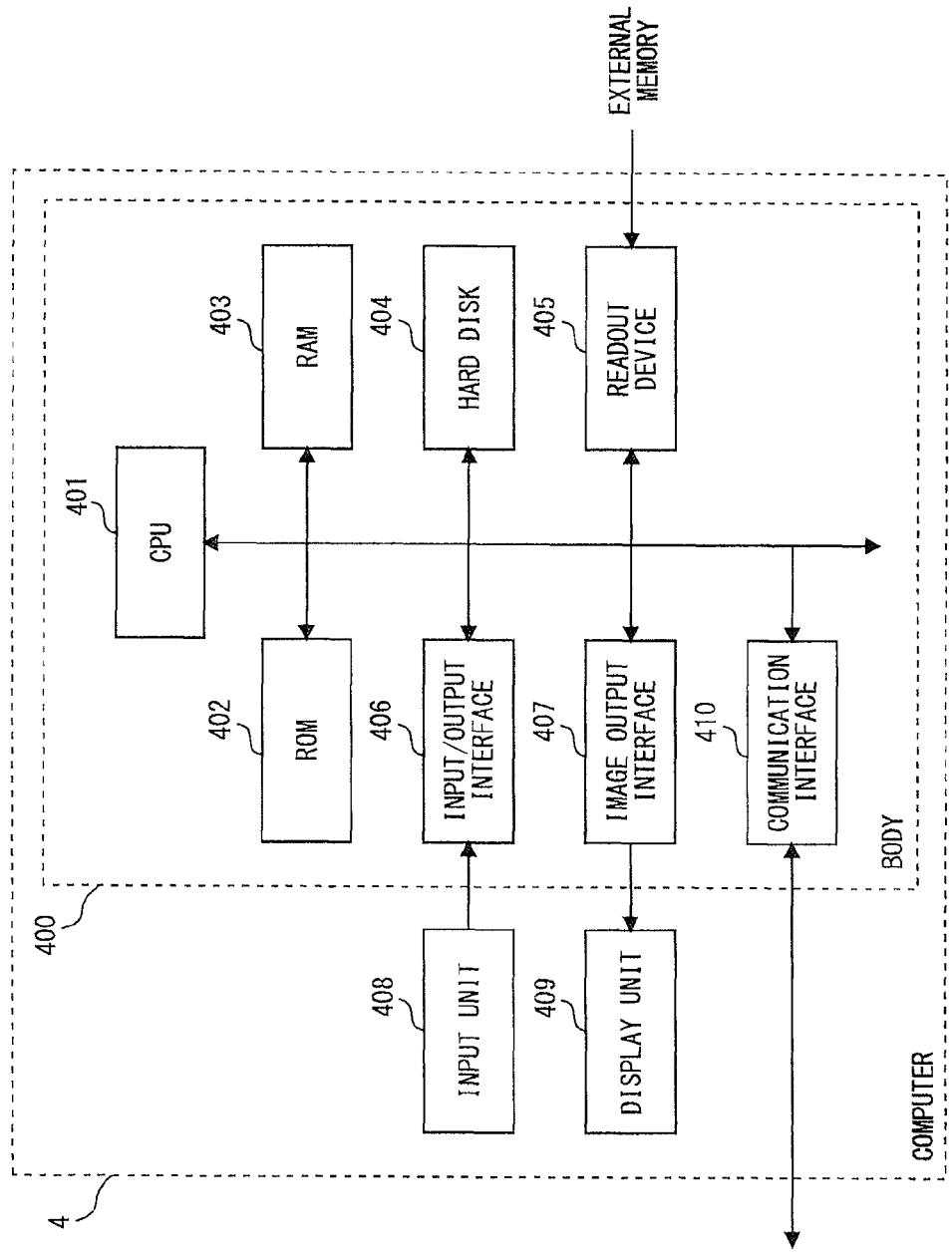
FIG. 7 is a block diagram showing a configuration of an information processing unit.

FIG. 7 is a block diagram showing a configuration of the information processing unit 4.

The information processing unit 4 is implemented by a personal computer, and includes a body 400, an input unit 408, and a display unit 409. The body 400 includes a CPU 401, a ROM 402, a RAM 403, a hard disk 404, a readout device 405, an input/output interface 406, an image output interface 407, and a communication interface 410.

The CPU 401 executes computer programs stored in the ROM 402 and computer programs loaded onto the RAM 403. The RAM 403 is used for reading computer programs stored in the ROM 402 and the hard disk 404. Further, the RAM 403 is also used as a work area for the CPU 401 when the CPU 401 executes these computer programs.

Various computer programs to be executed by the CPU 401 and data used in the execution of the computer programs, such as an operating system and application programs, are installed in the hard disk 404. That is, computer programs for causing the computer to function as an information processing apparatus according to the present embodiment are installed in the hard disk 404.

Further, a calibration curve used in calibration of sample measurement data described later is stored for each measurement item in the hard disk 404.

The readout device 405 is implemented by a CD drive, a DVD drive, or the like, and can read out computer programs and data stored in a storage medium. The input unit 408 implemented by a mouse and a keyboard is connected to the input/output interface 406, and by a user using the input unit 408, data is inputted in the information processing unit 4. The image output interface 407 is connected to the display unit 409 implemented by a CRT, a liquid crystal panel, or the like, and outputs video signals in accordance with image data, to the display unit 409. The display unit 409 displays an image, based on the inputted video signals. The communication interface 410 allows the information processing unit 4 to transmit/receive data to/from the measurement unit 3, the management server 5, and the client apparatus 6.

<Configuration of Management Server>

Figure 8:
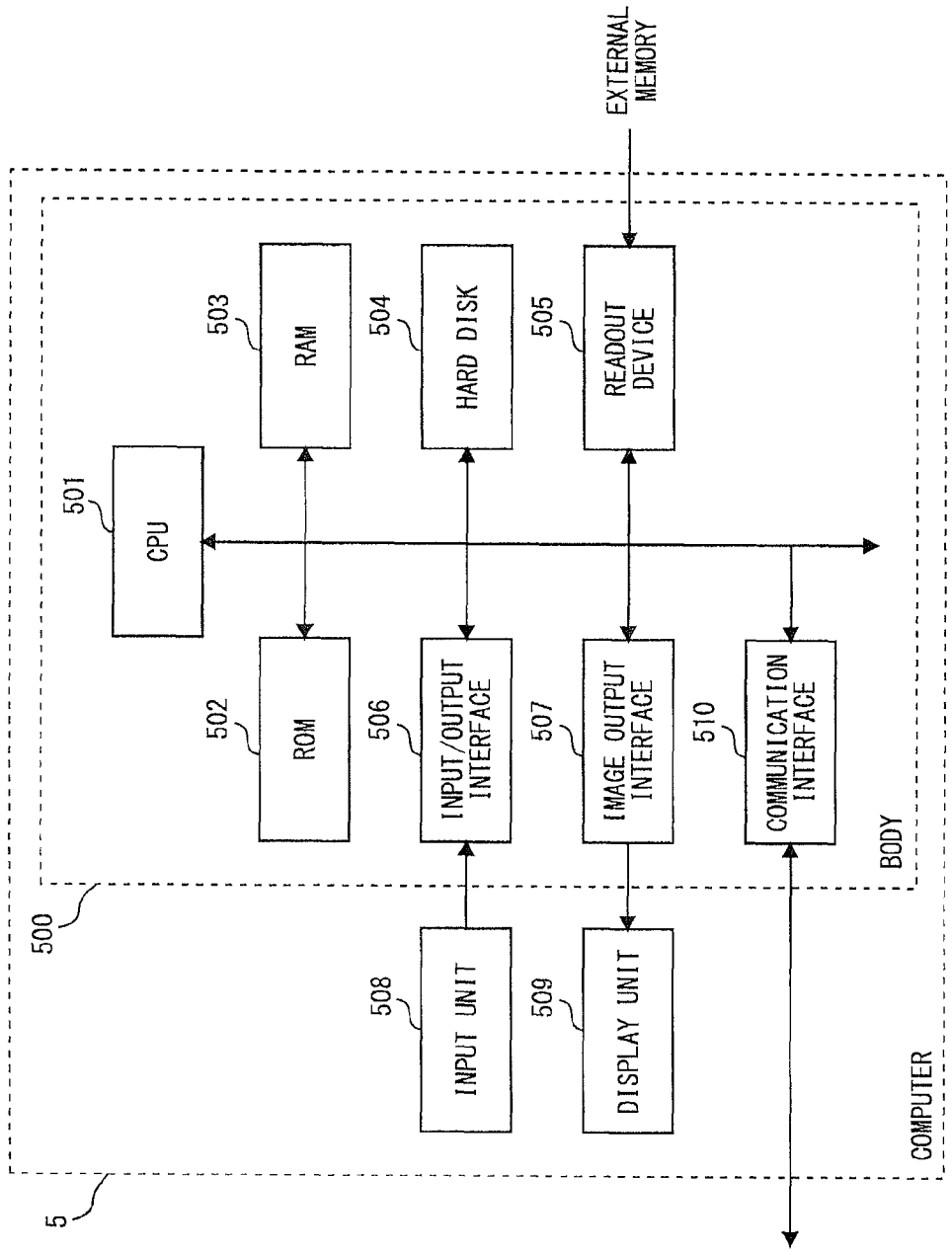
FIG. 8 is a block diagram showing a configuration of a management server.

FIG. 8 is a block diagram showing a configuration of the management server 5.

The management server 5 is implemented by a personal computer, and includes a body 500, an input unit 508, and display unit 509. The body 500 includes a CPU 501, a ROM 502, a RAM 503, a hard disk 504, a readout device 505, an input/output interface 506, an image output interface 507, and a communication interface 510.

The CPU 501 executes computer programs stored in the ROM 502 and executes computer programs loaded onto the RAM 503. The RAM 503 is used for reading out computer programs stored in the ROM 502 and the hard disk 504. Further, the RAM 503 is also used as a work area for the CPU 501 when the CPU 501 executes these computer programs.

Various computer programs to be executed by the CPU 501 and data used in execution of the computer programs, such as an operating system and application programs, are installed in the hard disk 504. That is, computer programs for causing the computer to function as a management server according to the present embodiment are installed in the hard disk 504.

The readout device 505 is implemented by a CD drive, a DVD drive, or the like, and can read out computer programs and data stored in a storage medium. The input unit 508 implemented by a mouse and a keyboard is connected to the input/output interface 506, and by a user using the input unit 508, data is inputted in the management server 5. The image output interface 507 is connected to the display unit 509 implemented by a CRT, a liquid crystal panel, or the like, and outputs video signals in accordance with image data, to the display unit 509. The display unit 509 displays an image, based on the inputted video signals. The communication interface 510 allows the management server 5 to transmit/receive data to/from the sample analyzer 2 and the client apparatus 6.

<Configuration of Client Apparatus>

The client apparatus 6 is implemented by a personal computer. The configuration of the client apparatus 6 is the same as that of the information processing unit 4 described above, except that not computer programs for causing the computer to function as the information processing unit 4, but computer programs for causing the computer to function as a client apparatus that accesses the management server and that is used to perform maintenance management operation for the sample analyzer 2 are installed in the hard disk. Therefore, description thereof will be omitted.

[Operation of Management System]

Hereinafter, operations performed by the management system according to the present embodiment will be described.

<Analysis Procedure for Each Sample>

First, an analysis procedure for a sample performed by the sample analyzer 2 will be described. The analysis procedure for a sample differs depending on the measurement items (PT, APTT, etc.) for the sample. The measurement items for the sample are specified by a measurement order. In the sample analyzer 2, it is possible for a user to register a measurement order, and also possible to receive a measurement order from a host computer not shown. That is, in the case where the user registers a measurement order, the user inputs the measurement order in the sample analyzer 2 by operating the input unit 408 of the information processing unit 4. In the case where a measurement order is received from the host computer, the user registers in advance the measurement order in the host computer.

A sample rack 60 accommodating a plurality of the sample containers 61 is set by the user in the pre-analysis rack holding area of the transport path 51. The sample rack 60 is moved rearward in the pre-analysis rack holding area, and then moved leftward in the transportation area. At this time, the bar code label attached to each sample container 61 is read by the sample bar code reader 52. A sample ID is stored in the bar code of each sample container 61. By using the read sample ID as a key, the information processing unit 4 obtains the measurement order of the sample from the host computer (not shown) connected thereto via a communication network.

Subsequently, the sample rack 60 is located at a predetermined position in the transportation area. When aspiration of the samples ends in the transportation area, the sample rack 60 is moved leftward in the transportation area, and then moved forward in the post-analysis rack holding area.

The first sample dispensing unit 21 aspirates a sample in a sample container 61 located at a predetermined sample aspirating position 53 in the transportation area of the transport path 51. The sample aspirated by the first sample dispensing unit 21 is discharged into a cuvette set in a cuvette holding hole 15a located at a sample discharging position 18 which is at a front position of the cuvette table 15.

The second sample dispensing unit 22 aspirates a sample contained in a cuvette at a sample aspirating position 19, or a sample in a sample container 61 located at a predetermined sample aspirating position 54 in the transportation area of the transport path 51. The sample aspirated by the second sample dispensing unit 22 is discharged into a cuvette set in the cuvette transporter 32. It should be noted that the second sample dispensing unit 22 can aspirate a diluent set in the diluent transporter 33. In this case, the sample dispensing unit 22 aspirates the diluent at a diluent aspirating position 37 before aspirating a sample, and then aspirates the sample at the sample aspirating position 19 or 54.

In the case where a measurement order including a plurality of measurement items for one sample has been obtained, the sample in the cuvette set in a cuvette holding hole 15a in the cuvette table 15 is subdivided into cuvettes, the number of the cuvettes corresponding to the number of measurement items. Each cuvette corresponds to one measurement item, and the subdivided sample in a cuvette is measured for the measurement item corresponding to that cuvette.

When the sample has been discharged (subdivided) into the cuvettes that have been accommodated in the cuvette transporter 32, the cuvette transporter 32 is driven rightward on the rail at a predetermined timing. Subsequently, a cuvette containing the sample set in the cuvette transporter 32 is gripped by the first catcher unit 26, and then set in a cuvette holding hole 16a in the heating table 16. The sample contained in the cuvette is heated for a time period corresponding to its measurement item in the heating table 16. For example, in the case where the measurement item is PT, the sample is heated for 3 minutes, and in the case where the measurement item is APTT, the sample is heated for 1 minute.

After the sample has been heated, a reagent is mixed into the sample. Whether the sample mixed with the reagent is measured by the detection unit 40 or heated again differs depending on the measurement item. For example, in the case where the measurement item is PT, a PT reagent is dispensed in the cuvette containing the heated sample, and then the resultant mixture is subjected to optical measurement in the detection unit 40.

In this case, the cuvette held in the cuvette holding hole 16a in the heating table 16 is gripped by the third catcher unit 28, and then located at a reagent discharging position 39a or 39b. Here, the second reagent dispensing unit 24 or the third reagent dispensing unit 25 aspirates a reagent in a predetermined reagent container 200 placed on the first reagent table 11 or the second reagent table 12, and discharges the reagent at the reagent discharging position 39a or 39b. Then, after the reagent has been discharged, the third catcher unit 28 sets the cuvette, into which the reagent has been discharged, in a holding hole 41 in the detection unit 40. Then, optical information of the measurement specimen contained in the cuvette is detected by the detection unit 40.

The case where the heated sample is mixed with a reagent and the resultant mixture is heated again will be described. In the case of a measurement item for which the sample is heated twice in this manner, the sample is heated for a predetermined time period in the heating table 16, and the second catcher unit 27 grips the cuvette containing the sample set in the holding hole 16a and moves it to a reagent discharging position 38. Here, the first reagent dispensing unit 23 aspirates a reagent in a predetermined reagent container 200 placed on the first reagent table 11 or the second reagent table 12, and discharges the reagent at the reagent discharging position 38. After the reagent has been discharged, the second catcher unit 27 agitates the cuvette and sets it in a cuvette holding hole 16a in the heating table again.

The cuvette held in the cuvette holding hole 16a in the heating table 16 is gripped by the third catcher unit 28, and then located at the reagent discharging position 39a or 39b. Here, the second reagent dispensing unit 24 or the third reagent dispensing unit 25 aspirates a reagent in a predetermined reagent container 200 placed on the first reagent table 11 or the second reagent table 12, and discharges the reagent at the reagent discharging position 39a or 39b. After the reagent has been discharged, the third catcher unit 28 sets the cuvette, into which the reagent has been discharged, in a holding hole 41 in the detection unit 40. Then, optical information of the measurement specimen contained in the cuvette is detected by the detection unit 40.

Measurement data (optical information) obtained by the detection unit 40 is transmitted to the information processing unit 4. The information processing unit 4 reads data of a calibration curve for the corresponding measurement item from the hard disk 404, and converts the measurement data by using the calibration curve. The converted measurement data is regarded as the final measurement result, and is stored in association with the sample information such as the sample ID, in a measurement result database (not shown) provided in the hard disk 404. Further, the measurement result is displayed on the display unit 409.

The cuvette for which detection by the detection unit 40 has been ended and which is no more needed is moved, being gripped by the third catcher unit 28, to a position directly above the disposal hole 35, and is discarded into the disposal hole 35. Also with respect to the cuvette held in a cuvette holding hole 15a in the cuvette table 15, when analysis therefor has been ended and the cuvette is no more needed, the cuvette table 15 is rotated and the cuvette is located at a position near the second catcher unit 27. The second catcher unit 27 grips the cuvette which is held in the cuvette holding hole 15a and is no more needed, and discards it into a disposal hole 36.

<Calibration Operation for Sample Analyzer>

Figure 9:
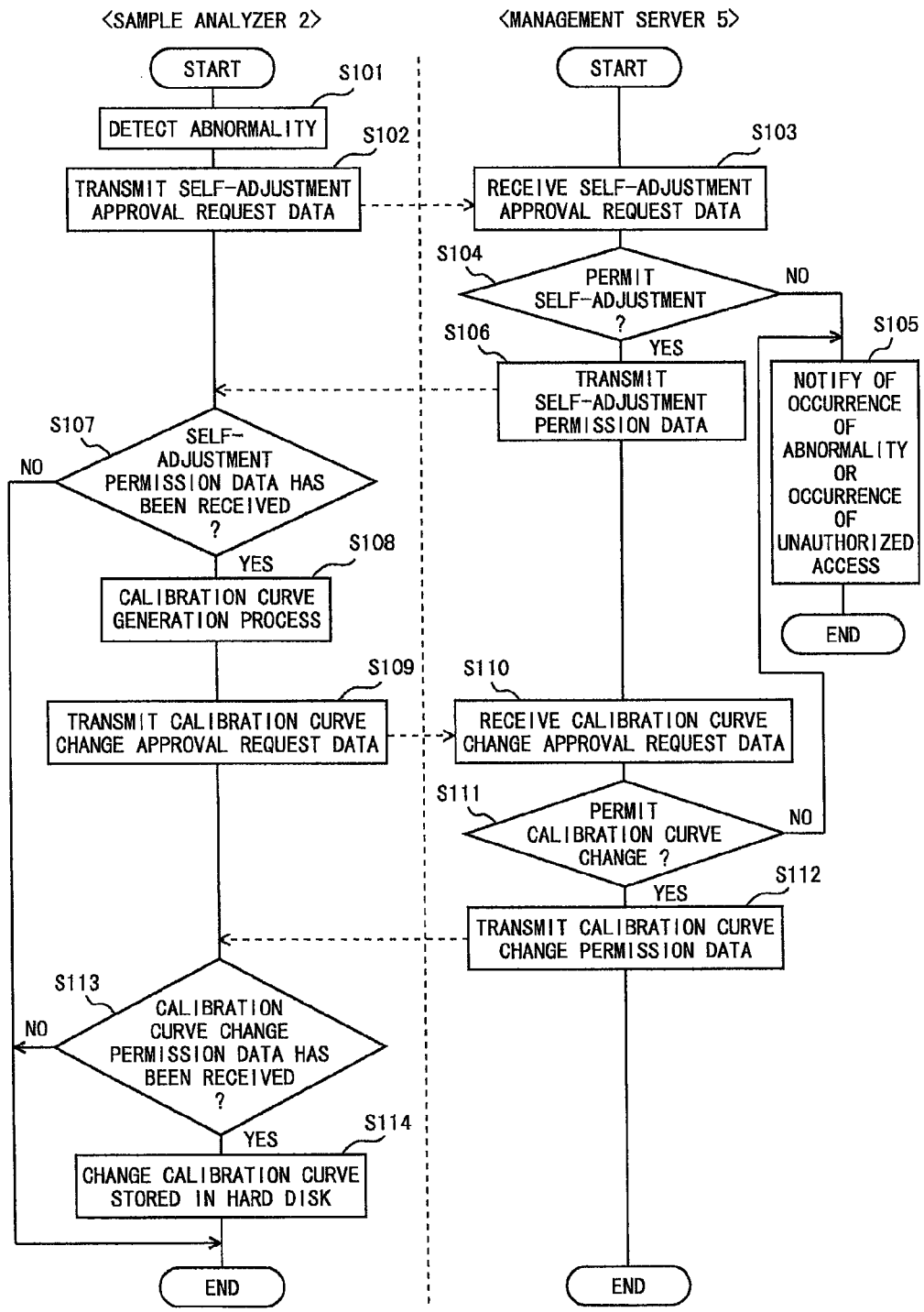
FIG. 9 is a flow chart showing the flow of a calibration operation performed in the management system according to embodiment 1.

Next, a calibration operation for the sample analyzer 2 will be described. FIG. 9 is a flow chart showing the flow of a calibration operation for the sample analyzer performed in the management system according to the present embodiment. The sample analyzer 2 measures a quality control substance in quality control, and when the measurement result is outside a limitation range for the quality control, the sample analyzer 2 detects this as abnormality. The CPU 401 detects this event of the detection of the abnormality, which is used by the sample analyzer 2 as a trigger for starting self-adjustment. In this manner, when abnormality has been detected in the sample analyzer 2 (step S101), the CPU 401 of the information processing unit 4 transmits, to the management server 5, self-adjustment approval request data including the authentication ID of the sample analyzer 2 stored in the hard disk 404 and abnormality information regarding the abnormality that has occurred (step S102). The abnormality information includes the date and time when the abnormality occurred, the type of the abnormality (in the above case, successive abnormalities in measurement results), data regarding the abnormality (such as measurement results), information of an error that occurred in the same time period in which the abnormality occurred, and the like.

The management server 5 receives the self-adjustment approval request data (step S103). The CPU 501 of the management server 5 determines whether to permit self-adjustment based on the received self-adjustment approval request data (step S104). The process of determining whether to permit the self-adjustment is performed by determining whether the received authentication ID is not an unauthorized one, and by checking whether the maintenance service under contract with the user includes self-adjustment of the sample analyzer. When the self-adjustment is not permitted (NO in step S104), the CPU 501 transmits, to the client apparatus 6, notification data that includes, for example, information specifying the sample analyzer in which the abnormality has occurred (apparatus ID, model name, facility name, and the like) and information indicating the type of the abnormality, or information indicating that an unauthorized access has occurred, thereby notifying a technician of occurrence of abnormality or occurrence of an unauthorized access (step S105). Accordingly, when notification of occurrence of abnormality has been made, a technician makes a telephone call to the user or visits the facility, whereby measures for eliminating the abnormality are taken. When notification of occurrence of an unauthorized access has been made, a technician contacts a security department or the like of the maintenance service provider, for example, whereby necessary measures against the unauthorized access are taken.

In step S104, when the self-adjustment has been permitted (YES in step S104), the CPU 501 transmits, to the sample analyzer 2, self-adjustment permission data indicating that the self-adjustment has been permitted (step S106). The self-adjustment permission data includes information necessary for performing a self-adjustment operation, such as the type of the self-adjustment, that is, information indicating generation of a calibration curve, information indicating a measurement item for which the calibration curve is to be generated, and the like.

The CPU 401 of the information processing unit 4 determines whether the self-adjustment permission data has been received (step S107). When the self-adjustment permission data has not been received (NO in step S107), the CPU 401 ends the process. On the other hand, when the self-adjustment permission data has been received (YES in step S107), the CPU 401 performs a calibration curve generation process (step S108).

Here, the calibration curve generation process will be described. The information processing unit 4 can cause a display unit 420 to display guidance information that explains the procedure of generating a calibration curve. In the calibration curve generation process, the CPU 401 causes the display unit 420 to display the guidance information. The user performs a calibration curve generation operation in accordance with the instruction by the guidance information.

First, the guidance information instructs the user to prepare calibrators. A calibrator is a standard substance having a known measurement value for a measurement item for which a calibration curve is to be generated. Hereinafter, the known measurement value of a calibrator will be referred to as a "calibration value". In the present embodiment, five calibrators respectively having different calibration values are used for generating a calibration curve. The user prepares five calibrators, causes a sample rack 60 to hold five sample containers 61 containing the respective calibrators in accordance with the guidance information, and sets the sample rack 60 in the pre-analysis rack holding area of the transport path 51. In this state, the user gives the information processing unit 4 an instruction to measure the calibrators.

When the instruction to measure the calibrators is given to the sample analyzer 2, the measurement unit 3 measures, in a similar procedure to the sample analysis procedure described above, each calibrator for the measurement item for which generation of a calibration curve has been instructed in the self-adjustment permission data. Measurement data (optical information) obtained by the detection unit 40 is provided to the information processing unit 4.

The CPU 401 of the information processing unit 4 generates a calibration curve for converting the measurement values of the respective calibrators provided from the detection unit 40 into the respective calibration values of the calibrators. The CPU 401 transmits, to the management server 5, calibration curve change approval request data including the authentication ID, the measurement values and the calibration values of the respective calibrators, and the generated calibration curve (step S109).

The management server 5 receives the calibration curve change approval request data (step S110). Based on the received calibration curve change approval request data, the CPU 501 of the management server 5 determines whether to permit calibration curve change (step S111). Whether to permit the calibration curve change is determined by determining whether the received authentication ID is not an unauthorized one, and by checking whether the maintenance service under contract with the user includes self-adjustment of the sample analyzer, and in addition, based on whether the measurement values of the calibrators included in the calibration curve change approval request data are within an acceptable range defined based on the calibration values of the calibrators. That is, when the measurement values are within the acceptable range, the calibration curve change is permitted, and when the measurement values are outside the acceptable range, the calibration curve change is not permitted.

When the calibration curve change is not permitted (NO in step S111), the CPU 501 transmits, to the client apparatus 6, notification data that includes, for example, information specifying the sample analyzer in which the abnormality has occurred (apparatus ID, model name, facility name, and the like) and information indicating the type of the abnormality, or information indicating that an unauthorized access has occurred, thereby notifying a technician of occurrence of abnormality or occurrence of an unauthorized access (step S105). Accordingly, when notification of occurrence of abnormality has been made, a technician makes a telephone call to the user or visits the facility, whereby measures for eliminating the abnormality are taken. When notification of occurrence of an unauthorized access has been made, a technician contacts a security department or the like of the maintenance service provider, for example, whereby necessary measures against the unauthorized access are taken.

In step S111, when the calibration curve change has been permitted (YES in step S111), the CPU 501 transmits, to the sample analyzer 2, calibration curve change permission data indicating that the calibration curve change has been permitted (step S112), and ends the process.

The CPU 401 of the information processing unit 4 determines whether the calibration curve change permission data has been received (step S113). When the calibration curve change permission data has not been received (NO in step S113), the CPU 401 ends the process. On the other hand, when the calibration curve change permission data has been received (YES in step S113), the CPU 401 changes the calibration curve stored in the hard disk 404 to the calibration curve generated in step S108 (step S114), and ends the process. Thus, the self-adjustment (generation of a calibration curve) of the sample analyzer 2 is completed.

<Pipette Position Adjustment Operation>

Figure 10:
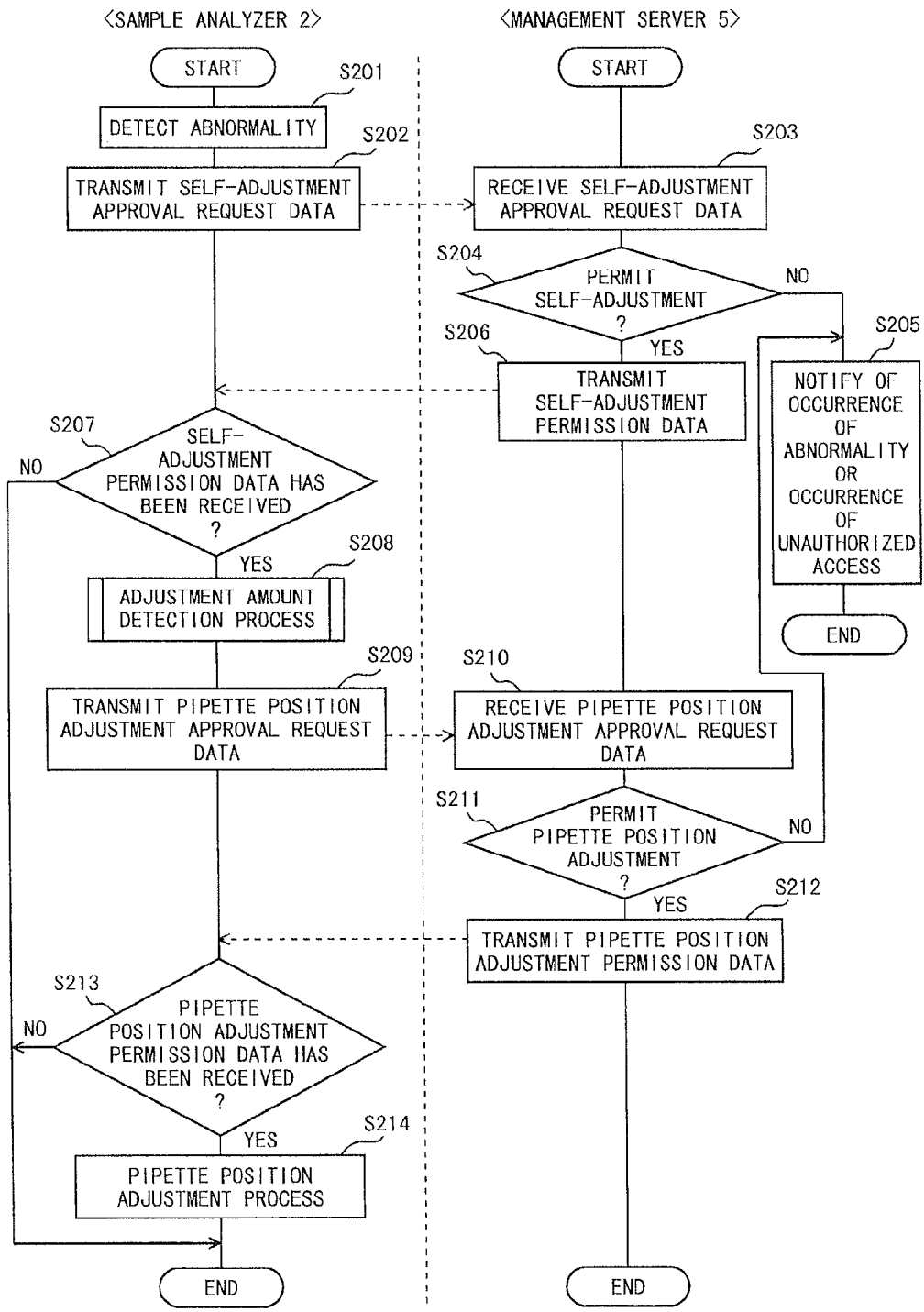
FIG. 10 is a flow chart showing the flow of a pipette position adjustment operation performed in the management system according to embodiment 1.

Next, a pipette position adjustment operation performed in the sample analyzer 2 will be described. FIG. 10 is a flow chart showing the flow of a pipette position adjustment operation performed in the management system according to the present embodiment. It should be noted that the case where the pipette position of the first reagent dispensing unit 23 is adjusted will be described here, but the pipette position in each of the first sample dispensing unit 21, the second sample dispensing unit 22, the second reagent dispensing unit 24, and the third reagent dispensing unit 25 is also adjusted through a similar operation.

The sample analyzer 2 can detect that a pipette has collided with an obstacle such as the wall of a cuvette, by means of the collision detection sensor section 323. In the case where the pipette P of the first reagent dispensing unit 23 dispenses a reagent into a cuvette located at the reagent discharging position 38, the pipette P having aspirated the reagent from a reagent container is caused to ascend, the arm 23b is then rotated by the driving section 23a, and the pipette P is positioned at the reagent discharging position 38. Subsequently, the pipette P is moved downward, and the tip of the pipette P is inserted into the cuvette. Here, due to displacement of the pipette P over time, or the like, in the case where the pipette P is not accurately positioned at the reagent discharging position 38, the pipette P will contact the wall of the cuvette or the like when the pipette P descends. Such a collision of the pipette P with an obstacle is detected by the collision detection sensor 170.

In this manner, when abnormality has been detected by the sample analyzer 2 (step S201), the CPU 401 of the information processing unit 4 transmits to the management server 5 self-adjustment approval request data including the authentication ID of the sample analyzer 2 stored in the hard disk 404 and abnormality information regarding the abnormality that has occurred (step S202). The abnormality information includes the date and time when the abnormality occurred, the type of the abnormality (in the above case, abnormality in the stop position of the pipette of the first reagent dispensing unit 23), data regarding the abnormality (such as an image taken by the camera 23d when the abnormality was detected), information of an error that occurred in the same time period in which the abnormality occurred, and the like.

The management server 5 receives the self-adjustment approval request data (step S203). Based on the received self-adjustment approval request data, the CPU 501 of the management server 5 determines whether to permit self-adjustment (step S204). The process of determining whether to permit the self-adjustment is performed by determining whether the received authentication ID is not an unauthorized one, and by checking whether the maintenance service under contract with the user includes self-adjustment of the sample analyzer. When the self-adjustment is not permitted (NO in step S204), the CPU 501 transmits, to the client apparatus 6, notification data that includes, for example, information specifying the sample analyzer in which the abnormality has occurred (apparatus ID, model name, facility name, and the like) and information indicating the type of the abnormality, or information indicating that an unauthorized access has occurred, thereby notifying a technician of occurrence of abnormality or occurrence of an unauthorized access (step S205). Accordingly, when notification of occurrence of abnormality has been made, a technician makes a telephone call to the user or visits the facility, whereby measures for eliminating the abnormality are taken. When notification of occurrence of an unauthorized access has been made, a technician contacts a security department or the like of the maintenance service provider, for example, whereby necessary measures against the unauthorized access are taken.

In step S204, when the self-adjustment has been permitted (YES in step S204), the CPU 501 transmits, to the sample analyzer 2, self-adjustment permission data indicating that self-adjustment has been permitted (step S206). The self-adjustment permission data includes information necessary for performing a self-adjustment operation, such as the type of the self-adjustment, that is, information indicating pipette position adjustment for the first reagent dispensing unit 23, and the like.

The CPU 401 of the information processing unit 4 determines whether the self-adjustment permission data has been received (step S207). When the self-adjustment permission data has not been received (NO in step S207), the CPU 401 ends the process. On the other hand, when the self-adjustment permission data has been received (YES in step S207), the CPU 401 performs an adjustment amount detection process (step S208).

Figure 11:
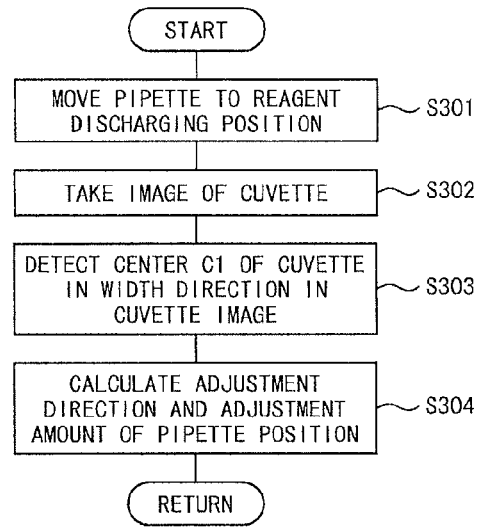
FIG. 11 is a flow chart showing a procedure of an adjustment amount detection process.

Here, the adjustment amount detection process will be described. FIG. 11 is a flow chart showing the procedure of the adjustment amount detection process. First, the CPU 401 controls the driving section 23a for the first reagent dispensing unit 23 to cause the pipette P to ascend to an upper limit position, and then causes the arm 23b to rotate, and causes the pipette P to move to the reagent discharging position 38 (step S301). The positional information of the reagent discharging position 38 is stored in the hard disk 404, as a moving amount (the pulse number of the rotation motor 231) of the arm 23b from its origin position to the reagent discharging position 38. That is, in step S301, by rotating the arm 23b from the origin position by the set moving amount, the pipette P is moved to the reagent discharging position 38. It should be noted that in the case where the position at which position adjustment should be performed is not the reagent discharging position 38 but a position for aspirating a reagent from a reagent container, the pipette P will be positioned at that position.

Next, the CPU 401 causes the camera 23d to take an image of the cuvette at the reagent discharging position 38 and obtains the image of the cuvette (step S302). At this time, when the cuvette is not at the reagent discharging position 38, the second catcher unit 27 is driven to position the cuvette at the reagent discharging position 38.

Figure 12:
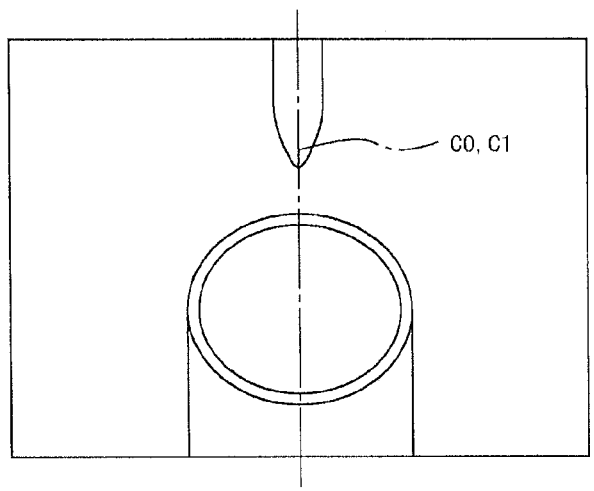
FIG. 12 is a schematic diagram showing an image of a cuvette when a pipette has not been displaced.
Figure 13:
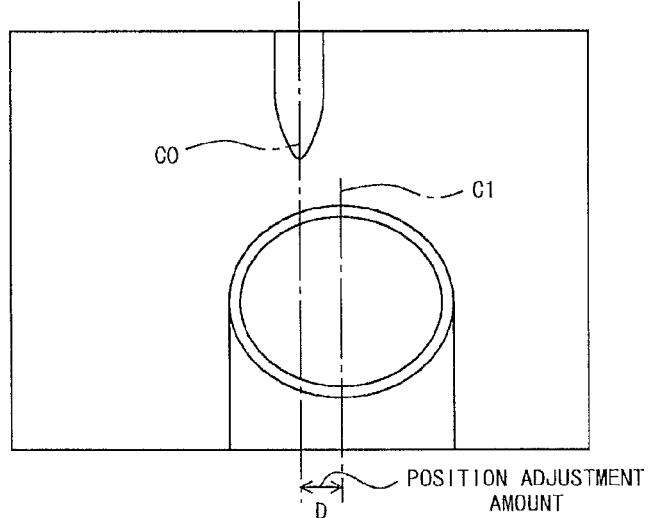
FIG. 13 is a schematic diagram showing an example of an image of a cuvette when a pipette has been displaced.

FIG. 12 is a schematic diagram showing an image of a cuvette when the pipette has not been displaced, and FIG. 13 is a schematic diagram showing an example of an image of a cuvette when the pipette has been displaced. The camera 23d is attached to the arm 23b such that the pipette P is always located at the middle in the left-right direction in an imaging area. As shown in FIG. 12, when the pipette has not been displaced, the center C1 of the cuvette in its width direction coincides with the center C0 of the image in the left-right direction. On the other hand, as shown in FIG. 13, when the pipette has been displaced, the center C1 of the cuvette in its width direction does not coincide with the center C0 of the image in the left-right direction. That is, the pipette P has been displaced by the distance D between the center C0 and the center C1. Moreover, the center C0 of the image is also the center position of the pipette P. Therefore, it is sufficient that the position of the pipette is adjusted by an adjustment amount that is the distance D, in a direction from the center C0 to the center C1.

The CPU 401 detects the center C1 of the cuvette in the width direction through image processing (step S303). Specifically, with respect to a predetermined pixel string extending in the horizontal direction of the image taken by the camera 23d (hereinafter, referred to as "cuvette image"), the image being a gradation image, the CPU 401 differentiates the pixel data (brightness values). The portion corresponding to the wall of the cuvette has higher brightness than the background. Thus, when differentiation is performed from left to right, derivative values become abruptly high at the boundary between the background and the wall of the cuvette at its left side, and derivative values become abruptly low at the boundary between the wall of the cuvette at its right side and the background. The CPU 401 detects a peak of the derivative values at the boundary between the background and the wall of the cuvette at its left side by using a predetermined positive first threshold value, and detects a peak of the derivative values at the boundary between the wall of the cuvette at its right side and the background by using a predetermined negative second threshold value. Further, the CPU 401 determines the middle position between the detected two peak positions, and sets this position as the center C1 of the cuvette in the width direction.

It should be noted that the image processing for determining the position of the center C1 of the cuvette in the width direction is not limited to the above method. The position of the wall of the cuvette may be detected by binarizing the cuvette image, or the position of the cuvette may be detected through pattern matching.

Next, the CPU 401 calculates an adjustment direction and an adjustment amount of the position of the pipette, based on the detected center C1 and the center C0 of the cuvette image (step S304). Specifically, when the direction from the center C0 to the center C1 is the right direction, the CPU 401 defines the clockwise direction in the rotation direction of the arm 23b as the adjustment direction. When the direction from the center C0 to the center C1 is the left direction, the CPU 401 defines the counter-clockwise direction in the rotation direction of the arm 23b as the adjustment direction. Further, the relationship between the distance D and the pulse number of the rotation motor 231 is stored in the hard disk 404, and thus, the CPU 401 derives, as an adjustment amount, a corresponding pulse number from the distance D between the center C0 and the center C1 detected in step S303.

After the process in step S304, the CPU 401 returns the process to the address for calling the adjustment amount detection process in the main routine.

After the adjustment amount detection process ends, the CPU 401 transmits, to the management server 5, pipette position adjustment approval request data including the authentication ID and the detected adjustment direction and adjustment amount (step S209).

The management server 5 receives the pipette position adjustment approval request data (step S210). The CPU 501 of the management server 5 determines whether to permit pipette position adjustment, based on the received pipette position adjustment approval request data (step S211). Whether to permit the pipette position adjustment is determined by determining whether the received authentication ID is not an unauthorized one, and by checking whether the maintenance service under contract with the user includes self-adjustment of the sample analyzer, and in addition, based on whether the adjustment amount included in the pipette position adjustment approval request data is within a predetermined acceptable range. That is, when the adjustment amount is within the acceptable range, the pipette position adjustment is permitted, and when the adjustment amount is outside the acceptable range, the pipette position adjustment is not permitted.

When the pipette position adjustment is not permitted (NO in step S211), the CPU 501 transmits, to the client apparatus 6, notification data that includes, for example, information specifying the sample analyzer in which the abnormality has occurred (apparatus ID, model name, facility name, and the like) and information indicating the type of the abnormality, or information indicating that an unauthorized access has occurred, thereby notifying a technician of occurrence of abnormality or occurrence of an unauthorized access (step S205). Accordingly, when notification of occurrence of abnormality has been made, a technician makes a telephone call to the user or visits the facility, whereby measures for eliminating the abnormality are taken. When notification of occurrence of an unauthorized access has been made, a technician contacts a security department or the like of the maintenance service provider, for example, whereby necessary measures against the unauthorized access are taken.

In step S211, when the pipette position adjustment has been permitted (YES in step S211), the CPU 501 transmits, to the sample analyzer 2, pipette position adjustment permission data indicating that the pipette position adjustment has been permitted (step S212), and ends the process.

The CPU 401 of the information processing unit 4 determines whether the pipette position adjustment permission data has been received (step S213). When the pipette position adjustment permission data has not been received (NO in step S213), the CPU 401 ends the process. On the other hand, when the pipette position adjustment permission data has been received (YES in step S213), the CPU 401 adjusts the pipette position in the adjustment direction and by the adjustment amount detected in step S208 (step S214), and ends the process. In step S214, the pipette position adjustment is performed by updating the positional information of the reagent discharging position 38 stored in the hard disk 404 with the adjustment direction and the adjustment amount detected in step S208. That is, when the rotation direction of the rotation motor 231 for rotating the arm 23b from its origin position to the reagent discharging position 38 is the same as the adjustment direction, the adjustment amount is added to the positional information (the pulse number of the rotation motor 231) stored in the hard disk 404. When the rotation direction of the rotation motor 231 for rotating the arm 23b from its origin position to the reagent discharging position 38 is opposite to the adjustment direction, the adjustment amount is subtracted from the positional information stored in the hard disk 404. In this manner, pipette position adjustment is performed. As a result, the self-adjustment (pipette position adjustment) of the sample analyzer 2 is completed.

According to the above configuration, the management system according to the present embodiment does not require complicated operations, such as a technician determining a command for remote-controlling the sample analyzer 2 and transmitting it to the sample analyzer 2, and thus, alleviates the burden on the technician, when compared with conventional management systems. Further, an adjustment amount due to an individual difference of the sample analyzer 2 is automatically detected, and this adjustment amount allows self-adjustment of the sample analyzer 2. Therefore, it is possible to perform appropriate adjustment for each sample analyzer. Further, if the sample analyzer 2 performs the self-adjustment on its own, based on determination by itself, whether appropriate adjustment is performed is not known, and thus reliability of measurement results cannot be ensured. The management system according to the present embodiment is configured such that, unless approval by the management server 5 is obtained, the sample analyzer 2 cannot perform the self-adjustment. Therefore, the sample analyzer 2 can perform the self-adjustment only when adjustment thereof is necessary, and thus, reliability of measurement results by the sample analyzer 2 is not impaired.

Embodiment 2

The configuration of a management system according to the present embodiment is similar to that of the management system 1 according to embodiment 1. Therefore, the same components are denoted by the same reference characters, and description thereof will be omitted.

Next, operations performed by the management system according to the present embodiment will be described.

Figure 14:
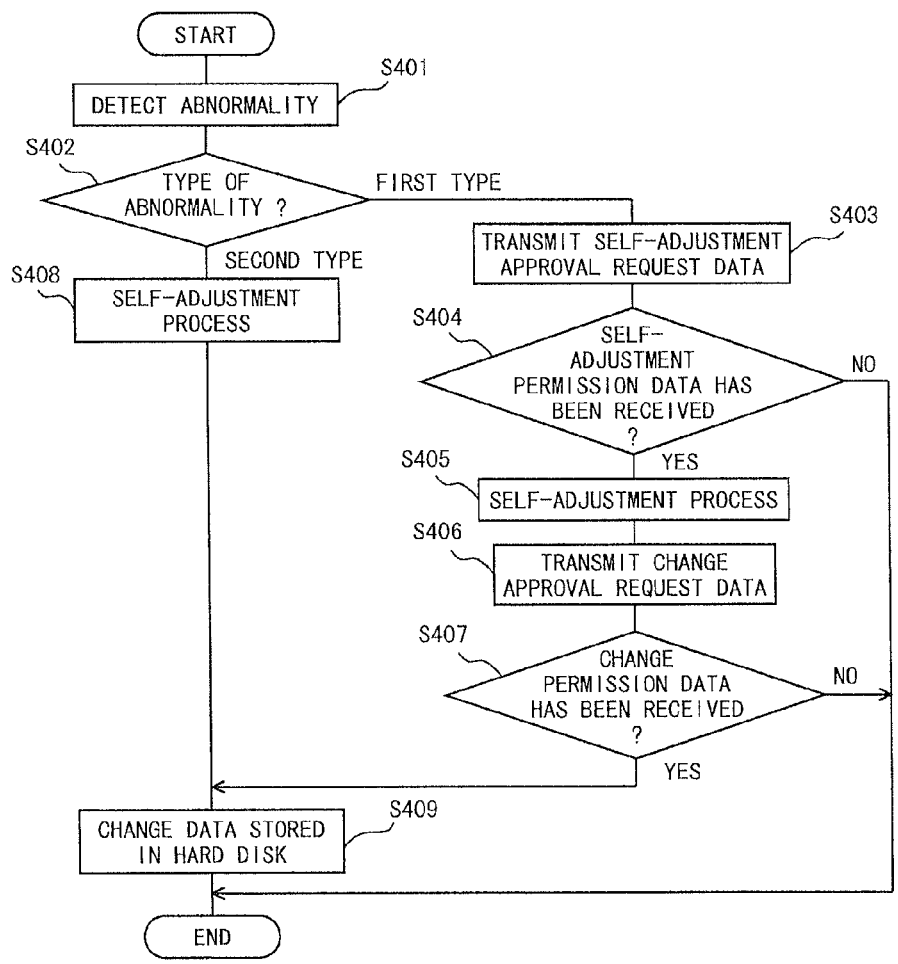
FIG. 14 is a flow chart showing the flow of a self-adjustment operation performed in a sample processing apparatus according to embodiment 2.

FIG. 14 is a flow chart showing the flow of a self-adjustment operation performed by a sample analyzer according to the present embodiment. When the sample analyzer 2 has detected abnormality, the CPU 401 detects the event of this detection of the abnormality, which is used as a trigger for the self-adjustment operation. The abnormality includes the quality control abnormality and the pipette drive abnormality as described in embodiment 1 above, and the like.

As described above, when abnormality has been detected in the sample analyzer 2 (step S401), the CPU 401 of the information processing unit 4 determines the type of the detected abnormality (step S402). Abnormalities that occur in the sample analyzer 2 include abnormality that greatly affects a sample analysis result, and abnormality that scarcely affects a sample analysis result. For example, abnormality in a quality control result may require re-generation of the calibration curve, and this directly affects a sample analysis result. On the other hand, abnormality relating to mechanical arrangement or drive, such as pipette drive failure, bar code reading abnormality, and catcher drive abnormality, scarcely affects a sample analysis result. In the process of step S402, it is determined whether the abnormality detected in step S401 is abnormality that greatly affects a sample analysis result (hereinafter referred to as "first type abnormality") or abnormality that scarcely affects a sample analysis result (hereinafter referred to as "second type abnormality"). More specifically, in the hard disk 404, with respect to each abnormality, information indicating that the abnormality is the first type abnormality or the second type abnormality is stored in association with a corresponding error code. When abnormality has been detected, the above information in the hard disk 404 is referred to, and which of the first type abnormality and the second type abnormality corresponds to the error code of the detected abnormality is specified.

In step S402, when it has been determined that the type of the detected abnormality is the first type ("first type" in step S402), the CPU 401 transmits self-adjustment approval request data to the management server 5 (step S403). The management server 5 receives the self-adjustment approval request data and determines whether to permit self-adjustment. When permitting the self-adjustment, the management server 5 transmits self-adjustment permission data to the sample analyzer 2, and when not permitting the self-adjustment, the management server 5 notifies a technician of occurrence of abnormality or occurrence of an unauthorized access. It should be noted that the operation performed by the management server 5 is similar to the operation performed by the management server 5 described in embodiment 1, and therefore, detailed description thereof is omitted here.

The CPU 401 of the information processing unit 4 determines whether the self-adjustment permission data has been received (step S404). When the self-adjustment permission data has not been received (NO in step S404), the CPU 401 ends the process. On the other hand, when the self-adjustment permission data has been received (YES in step S404), the CPU 401 performs a self-adjustment process (step S405). The self-adjustment process is a process of determining an adjustment value for eliminating the first type abnormality described above, and is, for example, the process of generating a calibration curve described in embodiment 1.

When the self-adjustment process has been ended, the CPU 401 transmits, to the management server 5, change approval request data including the authentication ID and the adjustment value obtained through the self-adjustment process (step S406). The management server 5 receives the change approval request data and determines whether to permit change from the adjustment value set in the sample analyzer 2 to a new adjustment value. When permitting changing the adjustment value, the management server 5 transmits change permission data to the sample analyzer 2, and when not permitting changing the adjustment value, the management server 5 notifies a technician of occurrence of abnormality or occurrence of an unauthorized access.

The CPU 401 of the information processing unit 4 determines whether the change permission data has been received (step S407). When the change permission data has not been received (NO in step S407), the CPU 401 ends the process. On the other hand, when the change permission data has been received (YES in step S407), the CPU 401 changes the adjustment value stored in the hard disk to the adjustment value obtained through the self-adjustment process in step S405 (step S409), and ends the process.

Next, a case where the detected abnormality is the second type abnormality will be described. When it has been determined that the type of the detected abnormality is the second type in step S402 ("second type" in step S402), the CPU 401 does not request approval for self-adjustment from the management server 5, and performs a self-adjustment process (step S408). The self-adjustment process is a process for determining an adjustment value for eliminating the second type abnormality described above, and is, for example, the process of detecting a pipette position adjustment amount described in embodiment 1. In the case where the abnormality detected in step S401 is a bar code reading abnormality, a position adjustment amount for the bar code reader 31 is detected in the self-adjustment process. In the case where the abnormality detected in step S401 is a catcher drive abnormality, a position adjustment amount for the grip portion or the like of the catcher unit where the abnormality has occurred is detected.

When the adjustment value is obtained through the self-adjustment process, the CPU 401 changes the adjustment value stored in the hard disk to the adjustment value obtained through the self-adjustment process in step S405 (step S409), and ends the process.

In the above configuration, the management system according to the present embodiment requires approval by the management server 5 with respect to a self-adjustment that greatly affects a sample analysis result, and thus, it is possible to carefully perform the self-adjustment. Further, with respect to a self-adjustment that scarcely affects a sample analysis result, approval by the management server 5 is not required, and thus, it is possible to easily perform the self-adjustment.

Other Embodiments

In the above embodiments, the sample analyzer 2 having a self-adjustment function is a blood coagulation measurement apparatus. However, the present invention is not limited thereto. It may be configured such that a sample processing apparatus which processes samples, such as a blood cell counter, an immune analyzer, a gene amplification measurement apparatus, a biochemical analyzer, a urine qualitative analyzer, a urine formed element analyzer, or a blood smear preparation apparatus, performs self-adjustment.

Further, in the above embodiments, a configuration has been described in which self-adjustment is started by using an event of detection of abnormality as a trigger. However, the present invention is not limited thereto. Specifically, an operator manually inputs a predetermined command key provided in the sample analyzer, and the event of inputting this command is detected by the CPU 401 of the information processing unit 4, whereby instruction to start self-adjustment may be given. When an event in which the sample analyzer satisfies a predetermined condition has occurred (for example, when the number of analysis operations performed by the sample analyzer has reached a predetermined number, when the operating time period has reached a predetermined time period, or when a predetermined time period has elapsed since the preceding self-adjustment was performed), the CPU 401 of the information processing unit 4 detects the event, whereby self-adjustment may be started. Further, an apparatus, such as a management server, connected to a sample analyzer transmits to the sample analyzer a command that gives instruction to start self-adjustment, and the CPU 401 of the information processing unit 4 detects the event of receiving the command, whereby self-adjustment may be started.

Further, in the above embodiments, as a self-adjustment function of the sample analyzer 2, a configuration has been described in which the sample analyzer 2 performs generation of a calibration curve or position adjustment of a pipette that dispenses a reagent or a sample. However, the present invention is not limited thereto. Self-adjustment of other mechanisms may be performed. For example, it may be configured such that: a camera is attached to the tip of the arm of each of the first catcher unit to the third catcher unit so as to be able to take an image of the grip portion; and when a cuvette gripping failure by the grip portion has occurred, the camera takes an image of the grip portion where the cuvette gripping failure has occurred, and position adjustment of the grip portion is performed. Further, it may be configured such that: the bar code reader 31 is provided with an actuator such as a stepping motor to allow position adjustment; and when a bar code reading failure by the bar code reader has occurred, self-adjustment of the position of the bar code reader is performed.

Further, in the case where the sample analyzer having a self-adjustment function is configured to convert measurement data by using a set of calibration values and measurement values, such as in the case of a blood cell counter, a urine formed element analyzer, or the like, self-adjustment may be performed not by generating a calibration curve but by generating a conversion constant therefor.

Further, in the above embodiments, calibration for which the management server 5 automatically gives approval for self-adjustment has been described. However, the present invention is not limited thereto. It may be configured such that: the management server 5 transmits to the client apparatus 6 data for requesting approval for self-adjustment of the sample analyzer 2, and the client apparatus 6 requests approval for the self-adjustment from a technician in charge of maintenance; and when the approval has been obtained from the technician, the client apparatus 6 transmits self-adjustment permission data to the sample analyzer 2, thereby allowing the sample analyzer 2 to perform the self-adjustment.

The sample processing apparatus management system, the sample processing apparatus and the management apparatus according to the present invention are useful as a management system for a sample processing apparatus which process samples such as blood and urine, a sample processing apparatus, a management apparatus, and the like.

The invention claimed is:

1. A managing method for operating a sample processing apparatus using a management apparatus, the method comprising:
submitting a request from the sample processing apparatus to the management apparatus for approval of a self-adjustment of the sample processing apparatus before performing the self-adjustment;
upon approving the sample processing apparatus to perform the self-adjustment, informing the sample processing apparatus of approval of request from the management apparatus;
determining an adjustment by the sample processing apparatus and submitting the adjustment to the management apparatus requesting approval;
upon receipt of the adjustment from the sample processing apparatus, determining by the management apparatus if the adjustment is approvable;
upon approving the adjustment, informing the sample processing apparatus of approval of the adjustment from the management apparatus; and
performing, at the sample processing apparatus, the self-adjustment based on the adjustment approved by the management apparatus in response to the approval.

2. The management method according to claim 1, further comprising:
detecting an event for starting the self-adjustment by the sample processing apparatus,
wherein the request of approval is made when the event is detected.

3. The management method according to claim 2, wherein detecting the event includes detecting an abnormality in the sample processing apparatus.

4. The management method according to claim 2, further comprising:
determining a type of the event by the sample processing apparatus,
wherein, when the type of the event is a type of an event for which the self-adjustment should be performed without waiting for the approval, the sample processing apparatus performs the self-adjustment without waiting for the approval.

5. The management method according to claim 1, wherein the sample processing apparatus is provided in a hospital or a test center.

6. The management method according to claim 1, wherein the management apparatus is provided in a maintenance service provider facility.

7. The management method according to claim 1, wherein the management apparatus is connected to a plurality of sample processing apparatuses.

8. The management method according to claim 1, wherein the management apparatus is connected to a client apparatus that is communicably connected the management apparatus.

9. A method for managing self-adjustment of a sample processing apparatus by a management server, the method comprising:
receiving, at the management apparatus, an approval request for the self-adjustment from a sample processing apparatus;
determining, by the management apparatus, whether to permit the sample processing apparatus to perform the self-adjustment and communicating with the sample processing apparatus to inform that the self-adjustment is permitted when the determination is positive;
receiving at the management apparatus an adjustment determined by the sample processing apparatus; and
determining by the management apparatus whether the adjustment is approvable and communicating with the sample processing apparatus to inform that the adjustment is approved when the determination is positive, wherein the sample processing apparatus performs the self-adjustment based on the adjustment approved by the management apparatus in response to an approval.

10. The method for managing self-adjustment of a sample processing apparatus according to claim 9, wherein the sample processing apparatus is provided in a hospital or a test center.

11. The method for managing self-adjustment of a sample processing apparatus according to claim 9, wherein the management apparatus is provided in a maintenance service provider facility.

12. The method for managing self-adjustment of a sample processing apparatus according to claim 9, wherein the management apparatus is connected to a plurality of sample processing apparatuses.

13. The method for managing self-adjustment of a sample processing apparatus according to claim 9, wherein the management apparatus is connected to a client apparatus that is communicably connected the management apparatus.

14. The method for managing self-adjustment of a sample processing apparatus according to claim 9, wherein the management apparatus is configured to generate an adjustment value for the sample processing apparatus.

15. A self-adjustment method for a sample processing apparatus, comprising:
determining an adjustment by the sample processing apparatus;
sending approval request data requesting approval for a self-adjustment from the sample processing apparatus to the management apparatus;
determining an adjustment by the sample processing apparatus and transmitting the adjustment to the management apparatus for approval; and
performing the self-adjustment by the sample processing apparatus, after the sample processing apparatus receives approval data from the management apparatus indicating the adjustment is approved by the management apparatus.

16. The self-adjustment method for a sample processing apparatus according to claim 15, wherein the sample processing apparatus is provided in a hospital or a test center.

17. The self-adjustment method for a sample processing apparatus according to claim 15, wherein the management apparatus is provided in a maintenance service provider facility.

18. The self-adjustment method for a sample processing apparatus according to claim 15, wherein the management apparatus is connected to a plurality of sample processing apparatuses.

19. The self-adjustment method for a sample processing apparatus according to claim 15, wherein the management apparatus is connected to a client apparatus that is communicably connected the management apparatus.

20. The self-adjustment method for a sample processing apparatus according to claim 15, wherein the management apparatus is configured to generate an adjustment value for the sample processing apparatus.

* * * * *